United States Patent
Ujibashi

(10) Patent No.: US 10,579,605 B2
(45) Date of Patent: Mar. 3, 2020

(54) INFORMATION PROCESSING DEVICE, METHOD, AND COMPUTER-READABLE RECORDING MEDIUM

(71) Applicant: FUJITSU LIMITED, Kawasaki-shi, Kanagawa (JP)

(72) Inventor: Yoshifumi Ujibashi, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 185 days.

(21) Appl. No.: 15/899,067

(22) Filed: Feb. 19, 2018

(65) Prior Publication Data
US 2018/0239789 A1     Aug. 23, 2018

(30) Foreign Application Priority Data
Feb. 20, 2017   (JP) ................. 2017-028893

(51) Int. Cl.
| | | |
|---|---|---|
| G06F 16/22 | (2019.01) | |
| G06F 3/06 | (2006.01) | |
| G06F 16/21 | (2019.01) | |
| G16B 20/00 | (2019.01) | |
| G16B 50/00 | (2019.01) | |

(52) U.S. Cl.
CPC .......... *G06F 16/221* (2019.01); *G06F 3/0604* (2013.01); *G06F 16/211* (2019.01); *G16B 20/00* (2019.02); *G16B 50/00* (2019.02)

(58) Field of Classification Search
CPC .... G06F 16/221; G06F 16/211; G06F 3/0604; G16B 50/00; G16B 20/00; G16B 50/30; G16B 20/20
See application file for complete search history.

(56) References Cited

FOREIGN PATENT DOCUMENTS

| JP | 1992-84272 | 3/1992 |
|---|---|---|
| JP | 2003-36190 | 2/2003 |

OTHER PUBLICATIONS

Implementation and Evaluation of Genome Type Processing for Disease-Causal Gene Studies on DBMS, pp. 494-497, Mar. 2017.*
Paila, Gemini: Integrative Exploration of Genetic Variation and Genome Annotations, pp. 1-8 (Year: 2013).*
Rohm, Data Management for High-Throughput Genomics, pp. 1-10, (Year: 2009).*

(Continued)

*Primary Examiner* — Albert M Phillips, III
(74) *Attorney, Agent, or Firm* — Fujitsu Patent Center

(57) ABSTRACT

A variant master table includes respective columns for variant ID, variant pattern, and pattern code. A composite primary key constraint for the variant master table is set by the columns for variant ID and pattern code. The respective processors reads variant information, verifies whether or not variant patterns for variant positions have been entered into the table, and for unentered variant patterns, attempts to insert a row of information into the table that includes the unentered variant pattern, a corresponding variant ID, and a pattern code allocated based on the variant master table. In cases in which the row of information violates a composite primary key constrain, the respective processor reattempts to insert an updated row of information in which the pattern code has been changed. The processors encode the variant information based on information entered into the variant master table.

18 Claims, 21 Drawing Sheets

(56) References Cited

OTHER PUBLICATIONS

The Variant Call Format (VCF) Version 4.2 Specification, pp. 1-28 (Year: 2015).*
Ameur, CanvasDB: a local database infrastructure for analysis of targeted—and whole genome re-sequencing projects, pp. 1-10 (Year: 2014).*
Ujibashi, Proposal of a Database Type and Aggregation Function for Accelerating Medical Genomics Study on RDBMS, pp. 672-673, Mar. 18, 2016.*

* cited by examiner

FIG.2

| INDIVIDUAL ID | V0 | V1 | V2 | ... | Vn |
|---|---|---|---|---|---|
| 0 | A/A | T/T | A/C | ... | G/G |
| 1 | A/C | T/T | A/C | ... | G/G |
| 2 | C/C | C/T | A/C | ... | G/T |
| 3 | C/C | C/C | A/C | ... | T/T |
| ... | | | | | |

FIG.8

```
CREATE TABLE variant_master_tbl (
    id          INTEGER,
    pat_code    INTEGER,
    pat_string  VARCHAR
    PRIMERRY KEY (id, pat_code)
);
```

FIG.15

VARIANT MASTER TABLE 26

| VARIANT ID | PATTERN CODE | VARIANT PATTERN |
|---|---|---|
| V0 | 0 (00$_2$) | A/A |
| V0 | 1 (01$_2$) | A/C |
| V0 | 2 (10$_2$) | C/C |
| V1 | 0 (00$_2$) | T/T |
| V1 | 1 (01$_2$) | C/T |
| V1 | 2 (10$_2$) | C/C |

↑ INSERT

106

| VARIANT ID | VARIANT PATTERN | VARIANT PATTERN CODE |
|---|---|---|
| .. | .. | .. |
| V$_1$ | C/C | 2 |
| .. | .. | .. |
| V$_m$ | A/C | 2 |
| V$_m$ | A/A | 3 |
| .. | .. | .. |

FIG.18
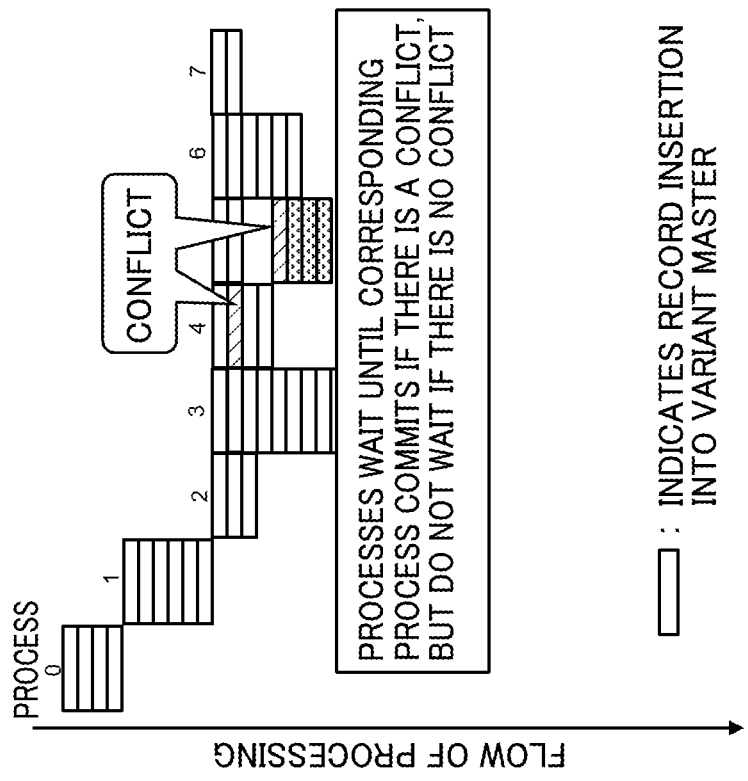
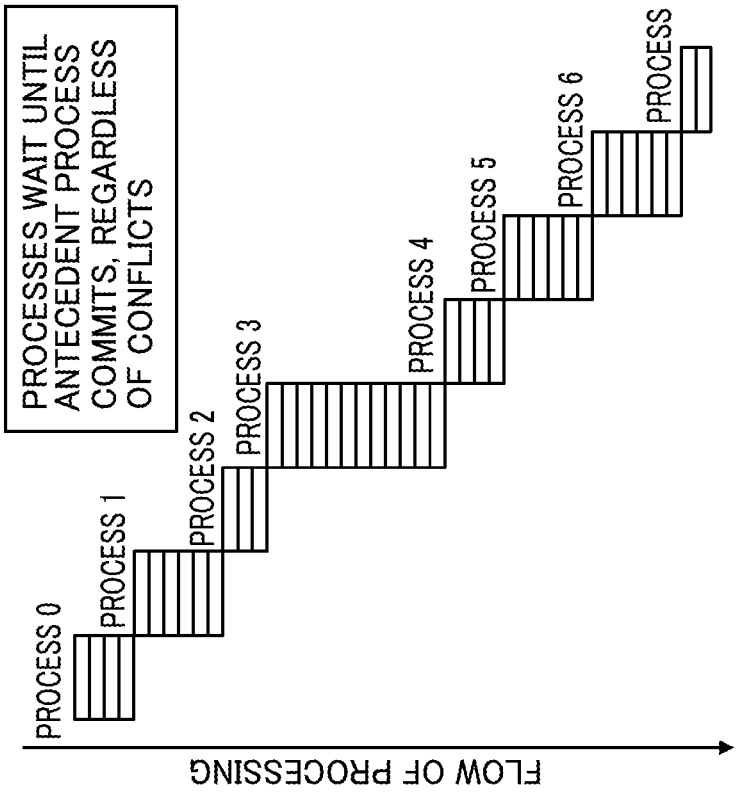

FIG.19

VARIANT MASTER TABLE (26)

| VARIANT ID | PATTERN CODE | VARIANT PATTERN |
|---|---|---|
| V0 | 0 ($00_2$) | A/A |
| V0 | 1 ($01_2$) | A/C |
| V0 | 2 ($10_2$) | C/C |
| V1 | 0 ($00_2$) | T/T |
| V1 | 1 ($01_2$) | C/T |
| V1 | 2 ($10_2$) | C/C |
| $V_m$ | 2 | A/A |

↑ INSERT

COMPOSITE PRIMARY KEY CONSTRAINT VIOLATION! (VARIANT ID AND PATTERN CODE OVERLAP)

(106)

| VARIANT ID | VARIANT PATTERN | PATTERN CODE |
|---|---|---|
| $V_1$ | C/C | 2 |
| .. | .. | .. |
| $V_m$ | A/C | 2 |
| $V_m$ | A/A | 3 |
| .. | .. | .. |

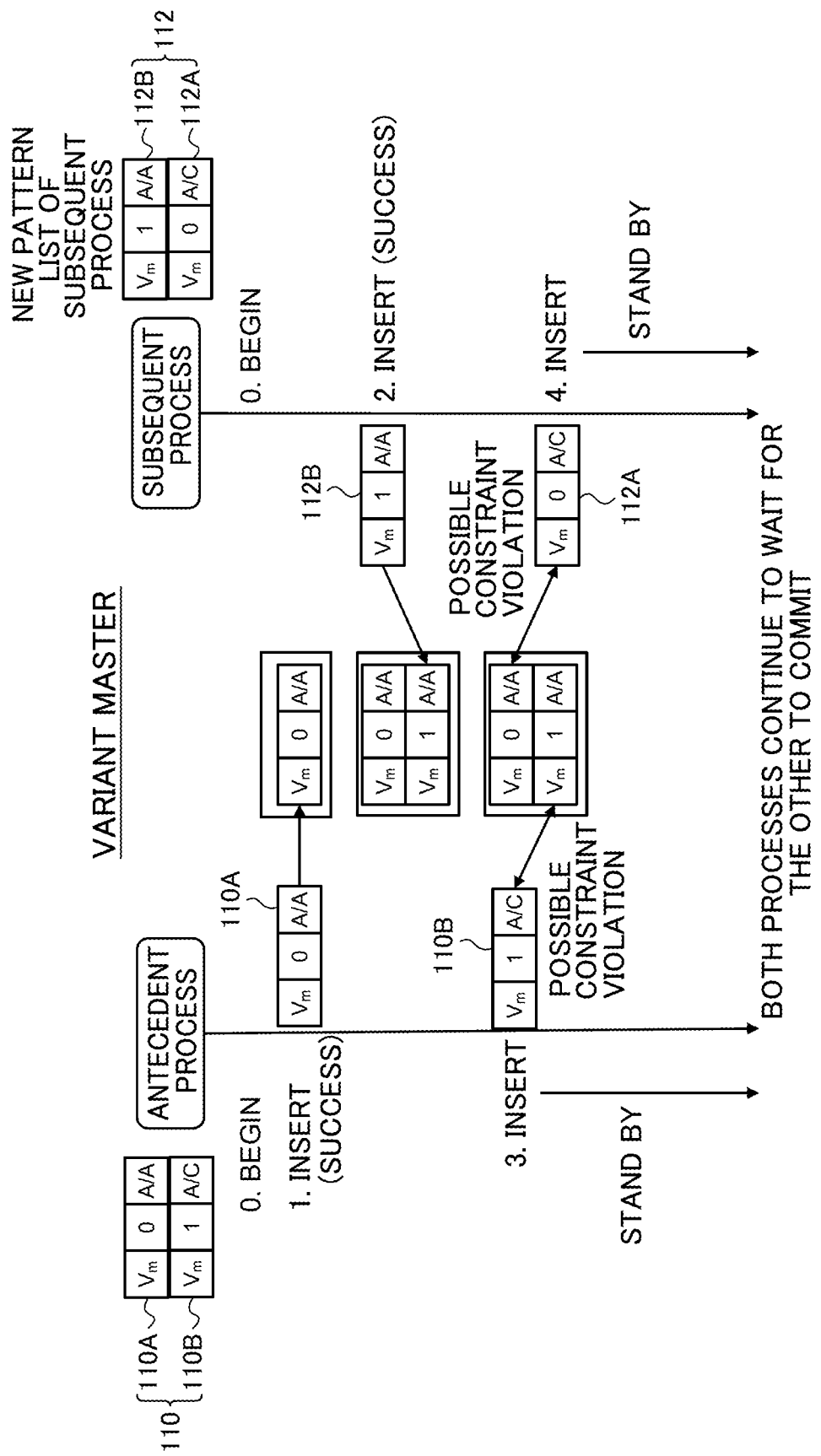

INFORMATION PROCESSING DEVICE, METHOD, AND COMPUTER-READABLE RECORDING MEDIUM

CROSS-REFERENCE TO RELATED APPLICATION

This application is based upon and claims the benefit of priority of the prior Japanese Patent Application No. 2017-028893, filed on Feb. 20, 2017, the entire content of which is incorporated herein by reference.

FIELD

The present invention relates to an information processing device, an information processing method, and a computer-readable recording medium.

BACKGROUND

A first technology is proposed that guarantees a constraint parameter such as a unique constraint of a database (hereafter, "DB"). In the first technology, counters are employed to count violations that occur and violations that are cleared at a given level (for example, per transaction) during DB operations, and when the value of the counter for each constraint parameter is 0 at the end of the given level, it is determined that there are no violations.

In a second technology, when DB difference information is entered into a difference table in preparation for undo processing, in cases in which plural items of difference information exist for the same primary key or for the same entry or attributes of a directory, only the first of such data is saved in a difference table. The second technology makes use of the fact that when plural items of difference information for the same primary key or for the same entry or attributes of a directory are sequentially entered into a difference table, the entry of a second, or subsequent, item of difference information will result in a primary key constraint violation.

RELATED PATENT DOCUMENTS

Japanese Patent Application Laid-Open (JP-A) No. H04-84272

Japanese Patent Application Laid-Open (JP-A) No. 2003-36190

SUMMARY

According to an aspect of the embodiments, an information processing device includes plural processors that operate in parallel. Each of the plural processors is configured to read variant information, and the variant information includes a variant pattern for each variant position and differs between the processors. A variant master table includes a column for variant position identifying information, a column for a variant pattern appearing at a respective variant position, and a column for a code allocated to the respective variant pattern. A composite primary key constraint for the variant master table is set by the column for the variant position identifying information and the column for the code. In cases in which a variant pattern at a variant position included in the read variant information has not been entered into the variant master table, the processors perform processing as follows. Namely, the respective processor attempts to insert, into the variant master table, a row of information including the unentered variant pattern, corresponding variant position identifying information, and a code allocated based on the variant master table. In cases in which the row of information for which insertion was attempted violates a composite primary key constraint for a row of information that had previously been inserted by another processor other than the respective processor, the respective processor reattempts to insert an updated row of information in which the code included in the row of information for which insertion was attempted has been changed. In addition, each of the processors encode the variant information based on information entered into the variant master table.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 2 is a schematic diagram illustrating examples of per-individual variant information stored in a variant information DB.

FIG. 8 illustrates an example command for instructing the creation of a variant master table.

FIG. 15 is a schematic diagram illustrating the insertion of a row of information included in a sorted list of information to be added into a variant master table.

FIG. 18 is a time chart illustrating an example of execution timings of processing performed by each processor (process) when an entire variant master table is locked and then updated (table locking), and in an exemplary embodiment (proposed method).

FIG. 19 is a schematic diagram illustrating an example of a situation in which a composite primary key constraint violation occurs.

FIG. 21 is a timing chart for explaining an issue that occurs when a list of information to be added to a variant master table is not sorted.

DESCRIPTION OF EMBODIMENTS

Figure 1:
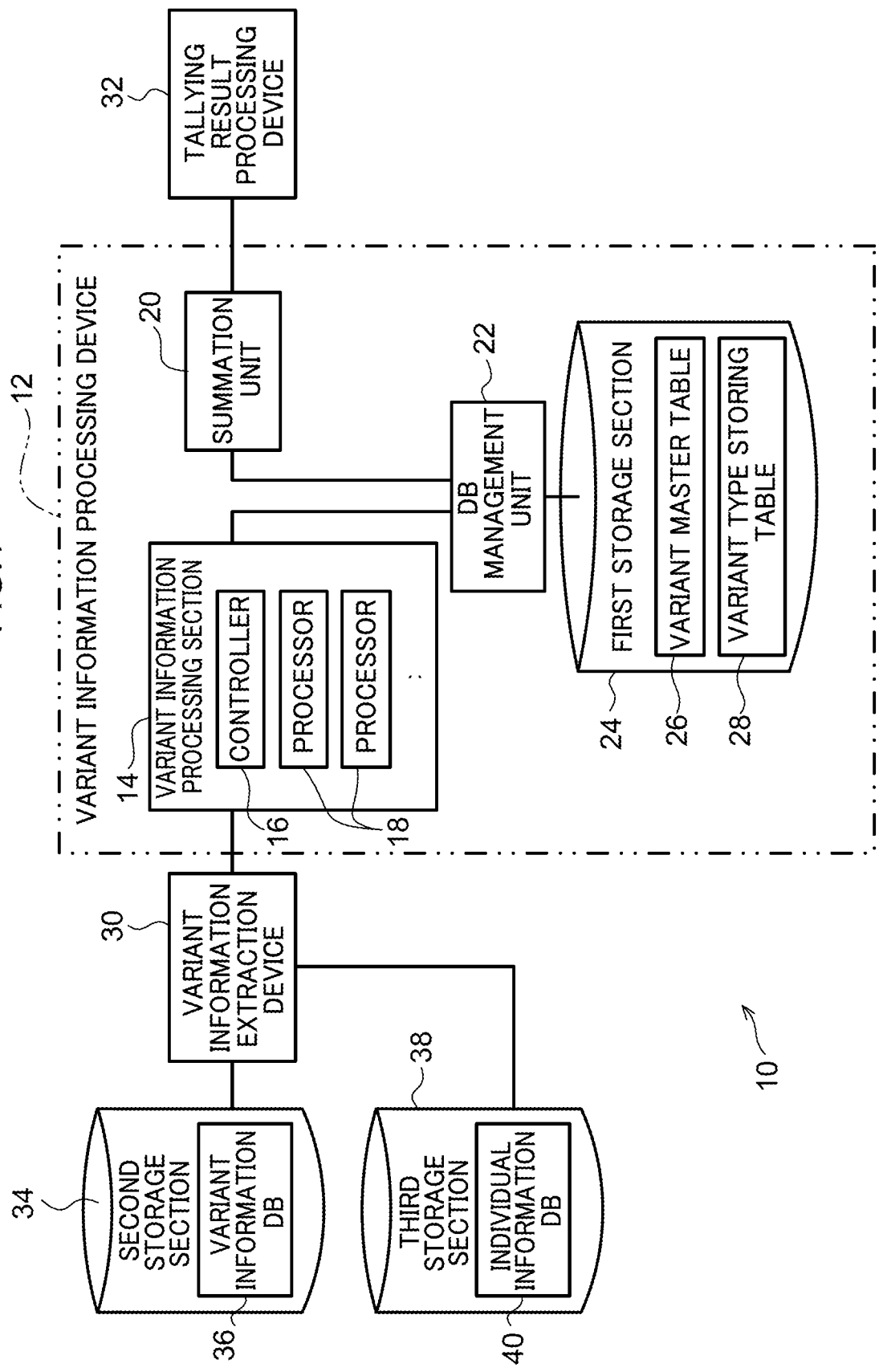
FIG. 1 is a schematic block diagram of a variant information analysis support system.

An exemplary embodiment of technology disclosed herein is described in detail below, with reference to the drawings. Note that in the following exemplary embodiment, as an example, explanation is given in which the positions of variations in genetic information (variant information) that are correlated with the incidence of a condition being analyzed, and the variant patterns thereof, are analyzed. The variant information analysis support system 10 illustrated in FIG. 1 includes a variant information processing device 12, which is an example of an information processing device of the present invention, a variant information extraction device 30, and a tallying result processing device 32.

The variant information extraction device 30 is connected to a second storage section 34 for storing a variant information DB 36, and to a third storage section 38 for storing an individual information DB 40. Variant information is entered into the variant information DB 36 on an individual basis for multiple individuals, in association with a respective individual ID (identifier). FIG. 2 illustrates an example of variant information 41 for plural individuals. In FIG. 2, per-individual variant information 42 corresponding to respective rows in the variant information 41 is information in which variant patterns at variant positions that have been extracted from the genetic information of a respective individual are arranged in sequence. In FIG. 2, V0 to Vn are variant IDs, which is an example of identifying information for individual variant positions, and "A/A", "T/T", "A/C", "G/G", and the like are variant patterns at the variant positions. Note that instead of just per-individual variant information 42, the complete genetic information of each individual may be stored in a DB.

Attribute information is entered into the individual information DB 40 on an individual basis for the multiple individuals for which variant information 42 has been entered into the variant information DB 36. Per-individual attribute information includes at least an individual ID, whether or not that individual has a condition, and in cases in which that individual has a condition, information indicating the condition. Per-individual attribute information may also include information such as the gender, age, height, weight, and lifestyle (for example, whether that individual has a smoking habit) of an individual.

Figure 3:
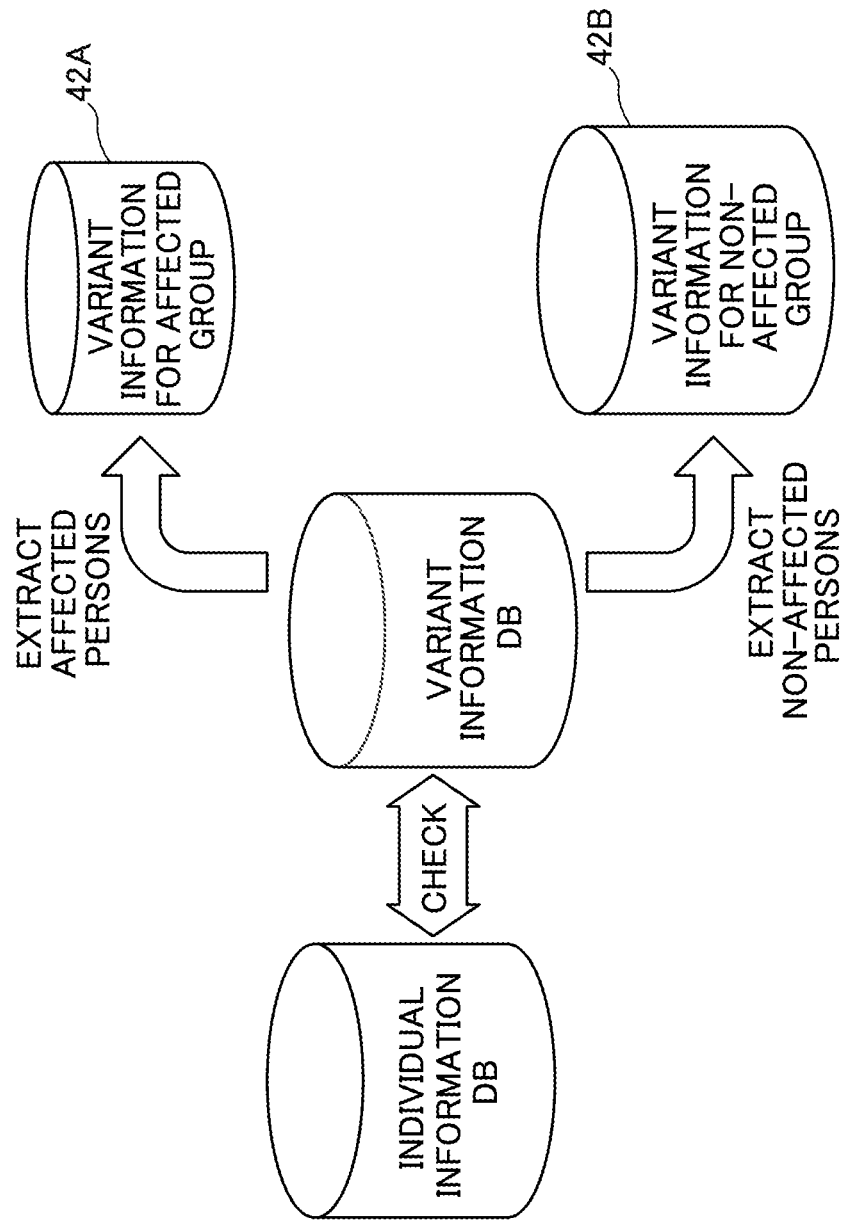
FIG. 3 schematically illustrates processing performed by a variant information extraction device.

When analyzing variant information, at a minimum, information designating a condition for analysis is input into the variant information extraction device 30 as a parameter for extracting variant information 42. Extraction parameters such as gender and age may also be added thereto. When an extraction parameter is input into the variant information extraction device 30, as illustrated in FIG. 3, the variant information DB 36 and the individual information DB 40 are checked, and per-individual variant information 42 for the group of individuals that match the input extraction parameter is read from the variant information DB 36. The group of individuals for which the per-individual variant information 42 is read is the set of individuals that all at least have the condition being analyzed, and such set is referred to below as an "affected group". The variant information extraction device 30 outputs the read per-individual variant information to the variant information processing device 12 as variant information 42A for the affected group.

The variant information extraction device 30 also reads per-individual variant information 42 for the group of individuals that do not match the input extraction parameter, or for the group of individuals that match only a subset of extraction parameters excluding that for condition, from the variant information DB 36. The group of individuals for which the per-individual variant information 42 is read is the set of individuals that all at least do not have the condition being analyzed, and such set is referred to below as a "non-affected group". The variant information extraction device 30 outputs the read per-individual variant information 42 as variant information 42B for the non-affected group.

Note that the variant information extraction device 30 may compile and output the extracted variant information 42 in a predetermined format. An example of such a predetermined format is the Variant Call Format (VCF). Although VCF is a common format for variant information, there is no limitation thereto, and variant information may be compiled into another format other than VCF.

As illustrated in FIG. 1, the variant information processing device 12 includes a variant information processing section 14, a tallying unit 20, a DB management unit 22, and a first storage section 24 for storing a variant master table 26 and a variant type storing table 28. The variant information processing section 14 further includes a controller 16 and plural processors 18. The DB management unit 22 performs processing for DB (such as the variant master table 26 in the present exemplary embodiment) operations in accordance with the input of commands stated in, for example, Structured Query Language (SQL).

The controller 16 of the variant information processing section 14 outputs a command to the DB management unit 22 instructing the creation of the variant master table 26. The variant master table 26 is accordingly created by the DB management unit 22 and stored in the first storage section 24. As explained in detail later, the variant master table 26 includes columns for variant IDs to indicate variant positions, variant patterns appearing at respective variant positions, and pattern code allocated to variant patterns. A composite primary key constraint for the variant master table 26 is set by the variant ID column and the pattern code column. The controller 16 controls activation of the plural processors 18 such that all of the variant information 42A for the affected group and the variant information 42B for the non-affected group that has been input from the variant information extraction device 30 is encoded and stored in the variant type storing table 28.

The plural processors 18 activated by the controller 16 perform the following variant information encoding processing in parallel. Namely, the processors 18 read the variant information 42 to be processed then verify whether or not the variant patterns for the variant positions included in the read variant information 42 have been entered into the variant master table 26. For each variant pattern not entered in the variant master table 26, the processors 18 output a command to the DB management unit 22 to insert a row of information (record) including the variant pattern, a corresponding variant ID, and a pattern code into the variant master table 26.

If a row of information to be inserted does not violate a composite primary key constraint for information already entered in the variant master table 26, the insertion of the row of information will succeed. However, in cases in which the row of information to be inserted violates a composite primary key constraint, the DB management unit 22 will give a notification of the constraint violation. In such cases, the processors 18 will output a command to the DB management unit 22 to insert, into the variant master table 26, an updated row of information in which the pattern code included in the row of information for which insertion had been previously attempted has been changed. In cases in which no unentered variant patterns are included in the variant information, or in cases in which the insertion of a row of information corresponding to an unentered variant pattern included in the variant information is successful, the processors 18 encode the variant information to be processed based on the variant master table 26. The processors 18 then store the encoded variant type information in the variant type storing table 28.

Figure 4:
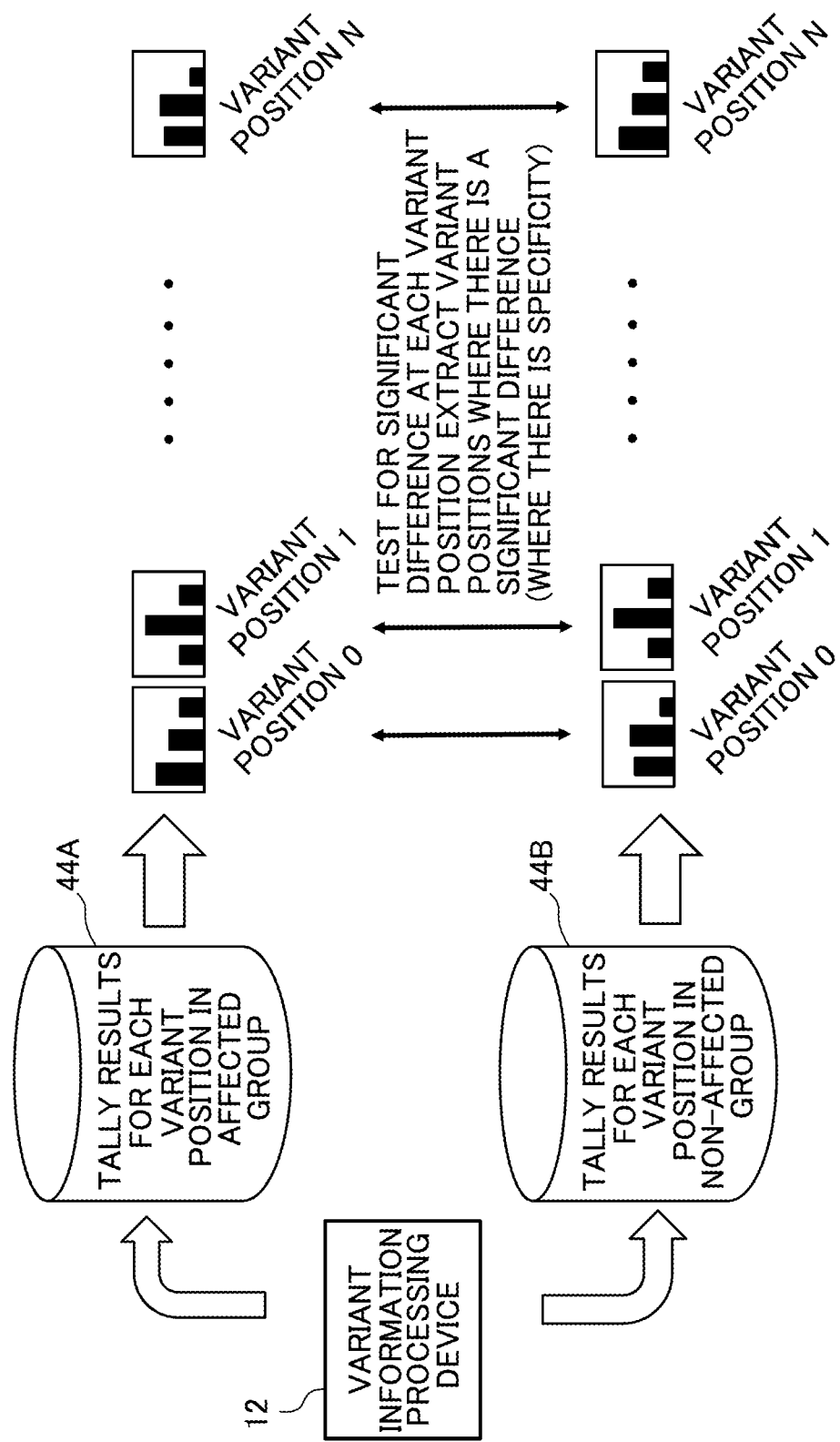
FIG. 4 schematically illustrates processing performed by a tallying result processing device.

The tallying unit 20 reads, via the DB management unit 22, variant type information that has been stored in the variant type storing table 28. The tallying unit 20 then tallies, per variant position, the number of appearances of each code for every code in the read variant type information, for both the affected group and the non-affected group. Based on the variant master table 26 stored in the first storage section 24, the tallying unit 20 also tallies, per variant position, the number of appearances of each variant pattern for every type of variant pattern in the individuals being processed, for both the affected group and the non-affected group. As illustrated in the example in FIG. 4, the tallying unit 20 then outputs both a tallying result 44A for each variant position in the affected group and a tallying result 44B for each variant position in the non-affected group to the tallying result processing device 32.

Figure 5:
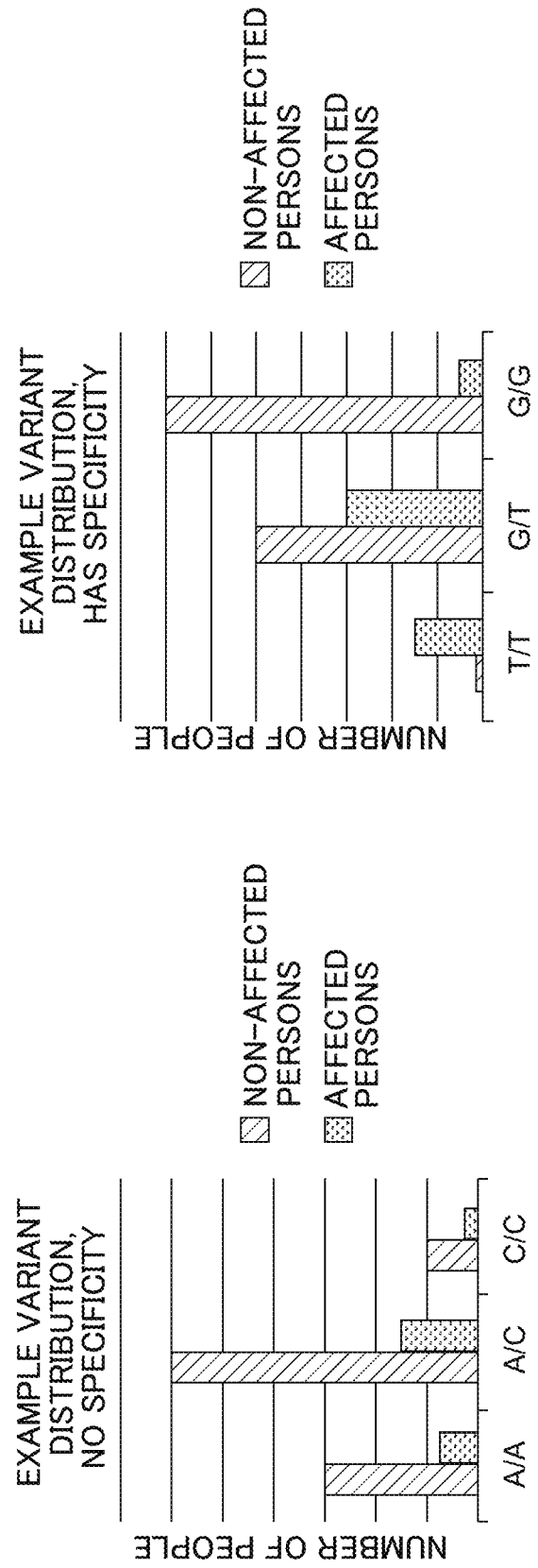
FIG. 5 schematically illustrates example variant pattern distributions at variant positions with no specificity and at variant positions with specificity.

The tallying result processing device 32 tests for whether or not there is a significant difference in the frequency of appearance of each variant pattern at respective variant positions (in the distribution of the number of appearances of each variant pattern) between the affected group and the non-affected group using a statistical method such as a chi-squared test on the input tallying results 44A, 44B. For example, as illustrated under "EXAMPLE VARIANT DISTRIBUTION, NO SPECIFICITY" in FIG. 5, for variant positions where the distributions of the number of appearances of respective variant patterns are similar between the affected group and the non-affected group, it can be determined that there is no significant difference, namely, that there is no correlation with incidence of the condition being analyzed. However, as illustrated under "EXAMPLE VARIANT DISTRIBUTION, HAS SPECIFICITY" in FIG. 5, for example, for variant positions where the distributions of the number of appearances of respective variant patterns are not similar between the affected group and the non-affected group, there is a significant difference, and it is thus possible that there is correlation with incidence of the condition being analyzed.

The tallying result processing device 32 assigns a ranking to the variant positions in the order of greatest significant difference in the distribution of the number of appearances of respective variant patterns, and outputs information for a predetermined number of the variant positions in descending order of their significant differences. Based on the information output from the tallying result processing device 32, an analyst analyzes the variant positions, and their respective variant patterns, where there is correlation with the incidence of the condition being analyzed.

Figure 6:
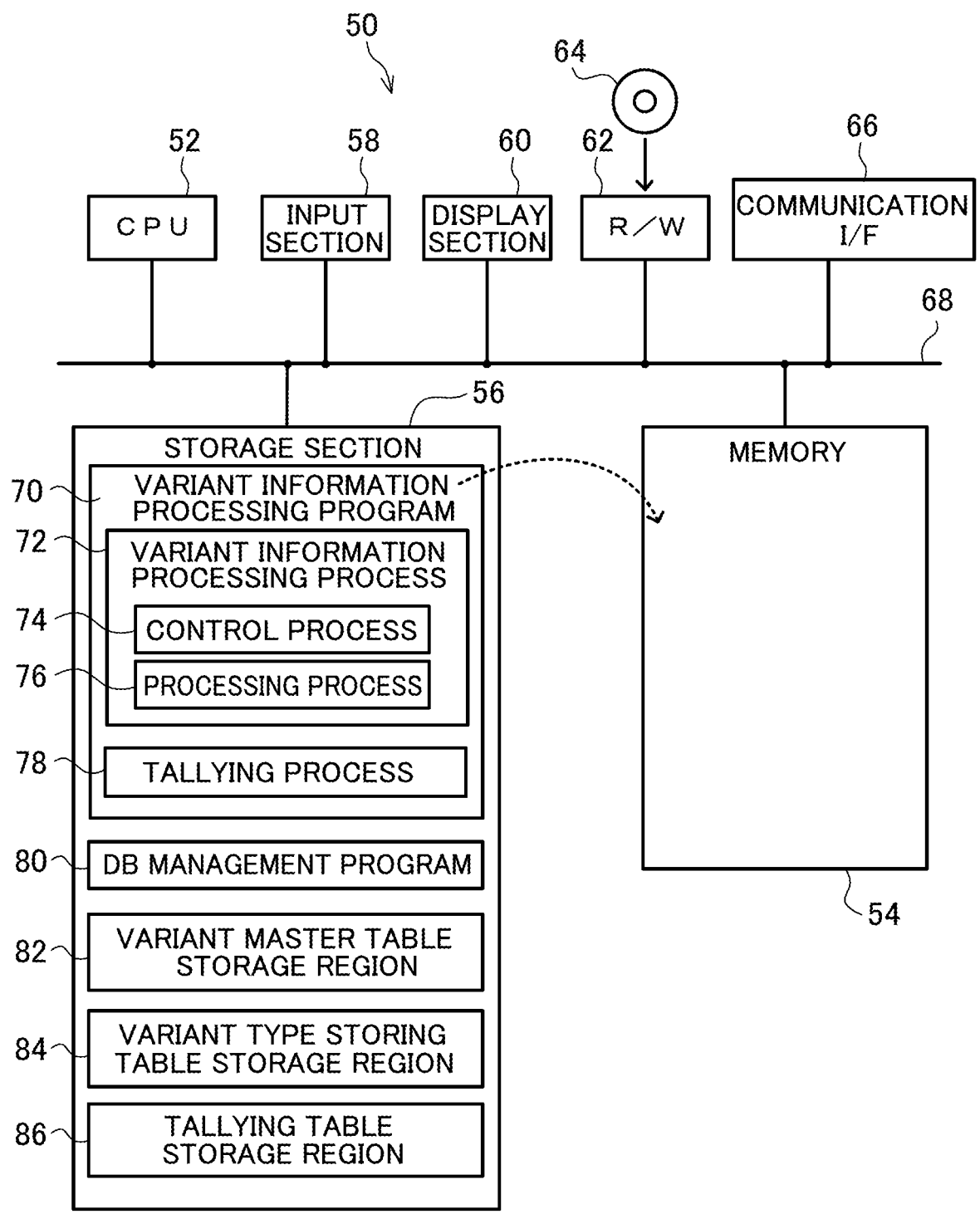
FIG. 6 is a schematic block diagram of a computer functioning as a variant information processing device.

In the present exemplary embodiment, the variant information processing device 12 is implemented by a computer 50 as illustrated in FIG. 6. The computer 50 includes a CPU 52, memory 54, a non-volatile storage section 56, an input section 58, a display section 60, a read/write device (R/W) 62 that reads data from and writes data to a recording medium 64, and a communication I/F section 66. The CPU 52, the memory 54, the storage section 56, the input section 58, the display section 60, the R/W 62, and the communication I/F section 66 are connected via a bus 68. The variant information processing device 12 is able to communicate with the variant information extraction device 30 and the tallying result processing device 32 over a network connected to the communication I/F section 66.

The storage section 56 may be implemented by a hard disk drive (HDD), a solid state drive (SSD), flash memory, or the like. The storage section 56 stores a variant information processing program 70 and a DB management program 80 for causing the computer 50 to function as the variant information processing device 12. The CPU 52 reads the variant information processing program 70 and the DB management program 80 from the storage section 56, expands the variant information processing program 70 and the DB management program 80 into the memory 54, then sequentially executes each of the processes included in the variant information processing program 70 and executes the DB management program 80.

The variant information processing program 70 includes a variant information processing process 72 and a tallying process 78. The variant information processing process 72 includes a control process 74 and a processing process 76.

The CPU 52 operates as the variant information processing section 14 illustrated in FIG. 1 by executing the variant information processing process 72. Namely, the CPU 52 operates as the controller 16 illustrated in FIG. 1 by executing the control process 74. The processing process 76 is configured so as to be reentrant. The CPU 52 also operates as the plural processors 18 illustrated in FIG. 1 by executing plural processing processes 76 in parallel. The CPU 52 operates as the tallying unit 20 illustrated in FIG. 1 by executing the tallying process 78. The CPU 52 operates as the DB management unit 22 illustrated in FIG. 1 by executing the DB management program 80.

The computer 50 functions as the variant information processing device 12 by executing the variant information processing program 70 and the DB management program 80 in this manner. The variant information processing program 70 is an example of an information processing program of technology disclosed herein.

The storage section 56 is provided with a variant master table storage region 82, a variant type storing table storage region 84, and a tallying table storage region 86. The variant master table 26 is stored in the variant master table storage region 82, and the variant type storing table 28 is stored in the variant type storing table storage region 84. The storage section 56 thereby functions as the first storage section 24 illustrated in FIG. 1.

Note that the variant information processing device 12 may, for example, be implemented by a semiconductor integrated circuit, and more specifically by an application-specific integrated circuit (ASIC).

Figure 7:
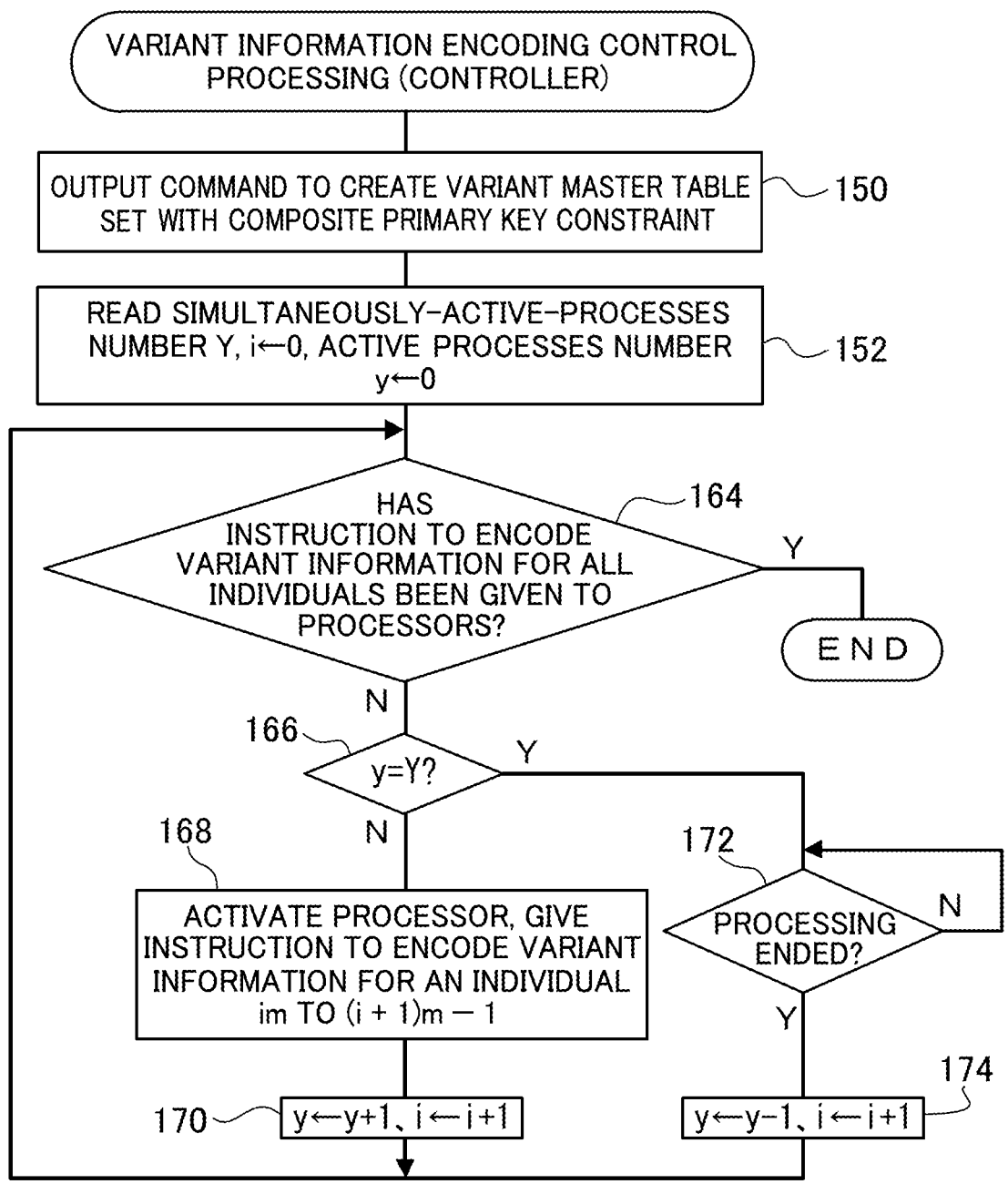
FIG. 7 is a flowchart illustrating an example of variant information encoding control processing.

Explanation follows regarding operation of the present exemplary embodiment, first, with regards to the variant information encoding control processing executed by the controller 16 of the variant information processing section 14, with reference to FIG. 7. At step 150, the controller 16 outputs a command to the DB management unit 22 to create the variant master table 26. The variant master table 26 includes columns for variant ID, variant pattern, and pattern code. A composite primary key constraint for the variant master table 26 is set by the variant ID column and the pattern code column.

FIG. 8 illustrates an example of the command output from the controller 16 to the DB management unit 22 at step 150. The command illustrated in FIG. 8 is a command that instructs the creation of the variant master table 26 (variant_master_tbl) including columns for variant ID (id), pattern code (pat_code), and variant pattern (pat_string). In this command, "PRIMARY KEY (id, pat_code)" means that a composite primary key constraint is to be set by the variant ID column and the pattern code column. Note that the command illustrated in FIG. 8 is merely exemplary, and this command may be modified as appropriate in accordance with the command format accepted by the DB management unit 22.

Figure 11:
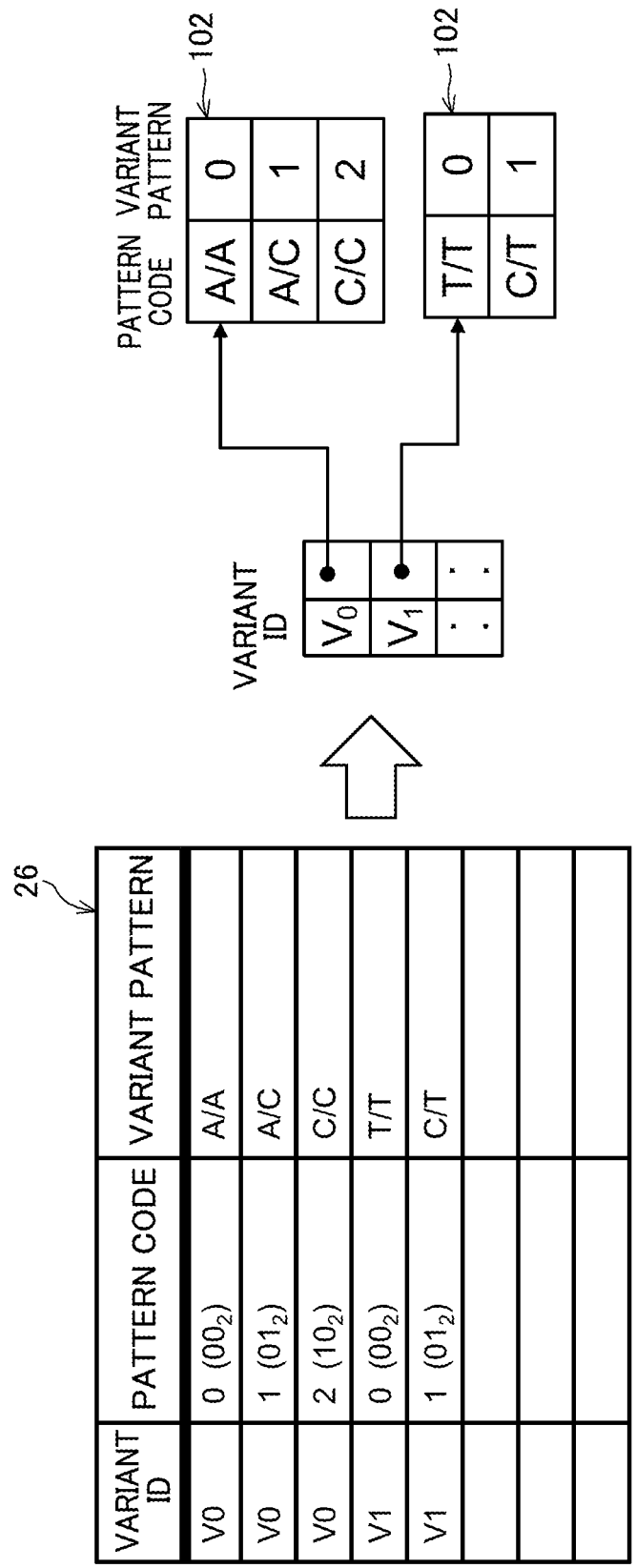
FIG. 11 is a schematic diagram for explaining processing to read a variant master table and expand the variant master table into memory.

When input with the above command, the DB management unit 22 creates a variant master table 26 such as illustrated in FIG. 11 and stores the variant master table 26 in the first storage section 24. Note that although FIG. 11 illustrates a state in which information has been entered into the variant master table 26, at this point the variant master table 26 is empty.

FIG. 11 does not explicitly illustrate the composite primary key constraint set for the variant master table 26. However, upon receiving a command to insert a row of information that includes a variant ID, a pattern code, and a variant pattern into the variant master table 26, the DB management unit 22 searches for records that have the same variant ID and pattern code as the row of information to be inserted. In cases in which such a record already exists in the variant master table 26, the DB management unit 22 notifies the command issuer that the row of information to be inserted violates a composite primary key constraint.

Next, at step 152, the controller 16 reads a simultaneously-active-processes number Y, set in advance, from the storage section 56 or the like. The controller 16 sets both a counter i, indicating the number of process (processor 18) activations, and a counter y, indicating the number of active processes, to 0. Note that the value of the simultaneously-active-processes number Y is set according to the capabilities of the computer 50.

Next, at step 164, the controller 16 makes a determination as to whether or not instruction to encode variant information 42 for all individuals has been given to the processors 18 by determining whether or not a value im has reached the total number of individuals. Processing transitions to step 166 in cases in which the determination of step 164 is negative. At step 166, the controller 16 makes a determination as to whether or not the counter y has reached the simultaneously-active-processes number Y.

Processing transitions to step 168 in cases in which the determination of step 166 is negative. At step 168, the controller 16 activates a processor 18, and instructs the activated processor 18 to encode the variant information 42 for an individual im to (i+1)m−1. The activated processor 18 (process) accordingly performs variant information encoding processing, described below, on the variant information 42 for an individual im to (i+1)m−1 (of m individuals).

Next, at step 170, the controller 16 increments the values of both the counter y and the counter i by 1, and processing returns to step 164. As described above, steps 168, 170 are repeated while the determinations of steps 164, 166 are both negative, thereby increasing the number of activated processors 18 (processes) executing the variant information encoding processing by 1 each time.

When the value of the counter y reaches the simultaneously-active-processes number Y, affirmative determination is made at step 166 and processing transitions to step 172. At step 172, the controller 16 makes a determination as to whether or not variant information encoding processing has ended for any of the activated processors 18 (processes). In cases in which the determination of step 172 is negative, step 172 is repeated until an affirmative determination is made. Processing transitions to step 174 in cases in which the determination of step 172 is affirmative. At step 174, the controller 16 decrements the value of the counter y by 1 and increments the value of the counter i by 1. Upon performing the processing of step 174, processing returns to step 164.

As a result of the above, the number of processors 18 (processes) executing the variant information encoding processing in parallel is maintained at or below the simultaneously-active-processes number Y. When instruction to encode variant information 42 for all individuals has been given to the processors 18, the value im reaches the total number of individuals, whereby an affirmative determination is made at step 164 and the variant information encoding control processing ends.

Figure 9:
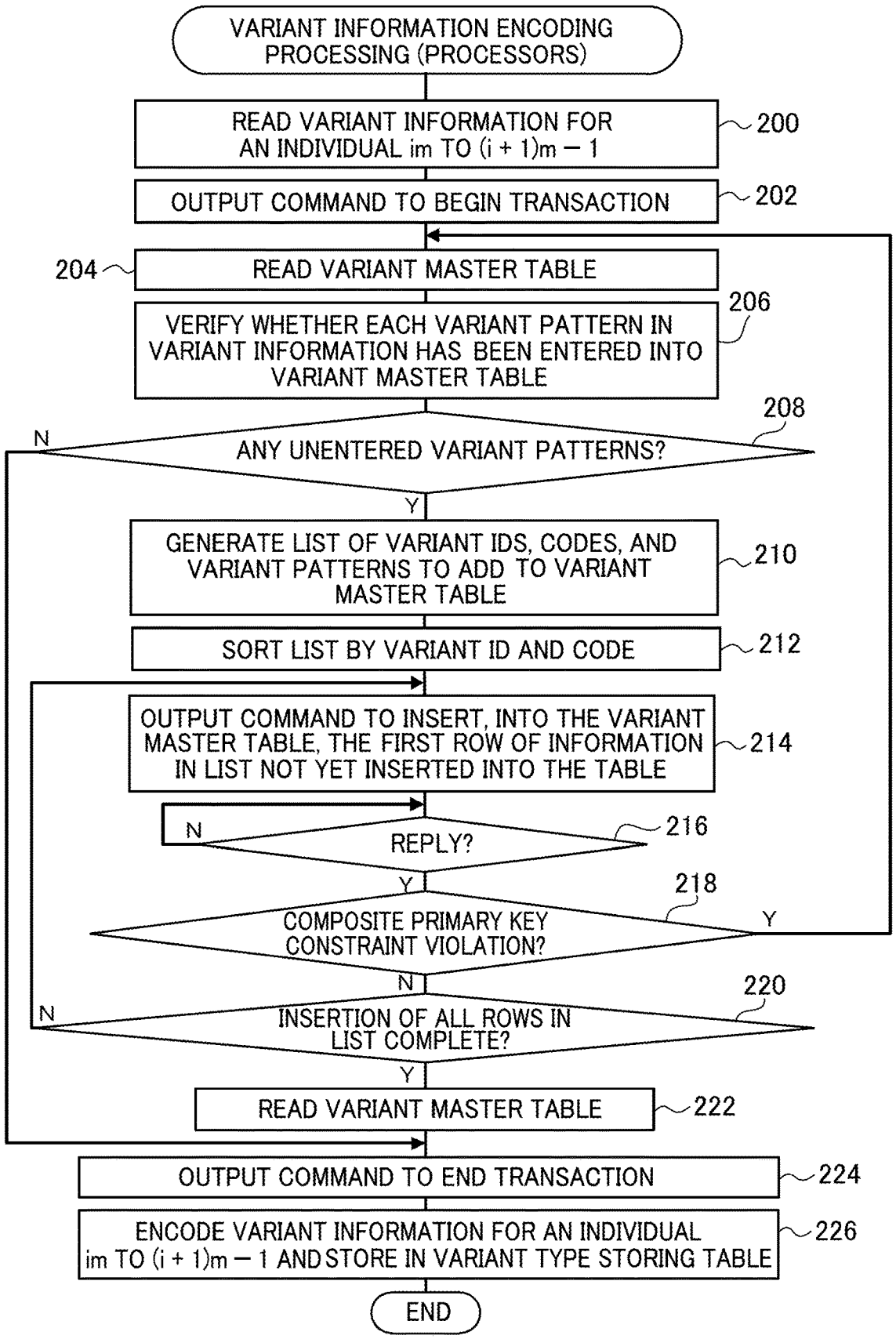
FIG. 9 is a flowchart illustrating an example of variant information encoding processing.
Figure 10:
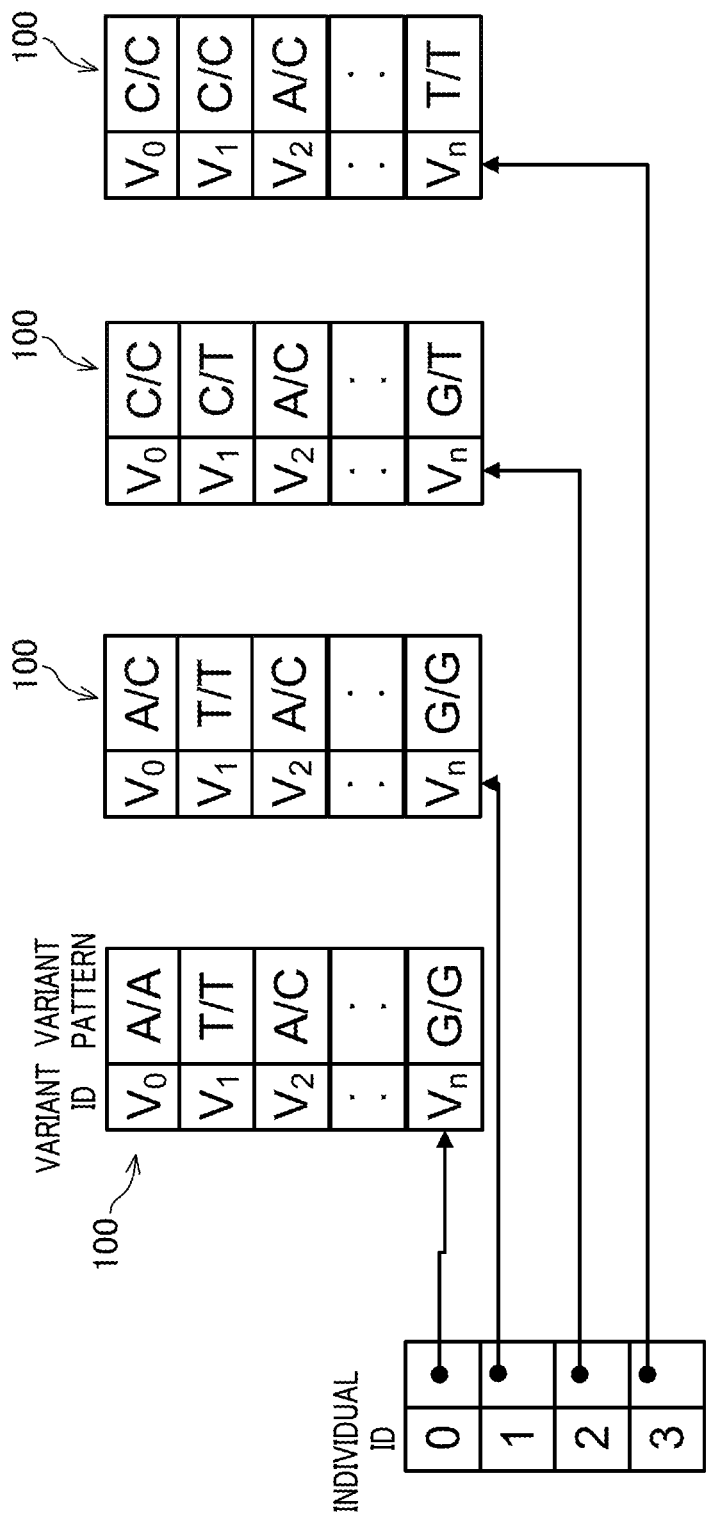
FIG. 10 is a schematic diagram for explaining processing to read variant information for plural individuals and expand the variant information into memory.

Explanation now follows regarding the variant information encoding processing executed by each processor 18 activated by the controller 16, with reference to FIG. 9. At step 200 of the variant information encoding processing, the processors 18 read the variant information 42 for individuals im to (i+1)m−1 for which notification has been given as being subject to processing from the controller 16, and the variant information 42 is expanded into the memory 54. As an example, FIG. 10 illustrates a case in which the variant information 42 for m=4 individuals has been read and expanded into the memory 54. Variant information 100 for a single individual expanded into the memory 54 includes a variant ID for each variant position (=V0 to Vn) and a variant pattern for each variant position. The variant information 100 of each individual is associated with a distinct individual ID.

At step 202, the processors 18 output a command to the DB management unit 22 to begin a respective transaction. Active processors 18 are recognized by transaction by the DB management unit 22. Note that although "BEGIN" is given herein as an example of a command to begin a transaction, there is no limitation thereto.

Next, at step 204, the processors 18 output a command to the DB management unit 22 to read the variant master table 26, and the variant master table 26 that is read via the DB management unit 22 is expanded into the memory 54. An example of a command to read the variant master table 26 is "SELECT id, pat_code, pat_string FROM variant_master_tbl". However, there is no limitation to this command, and this command may be modified as appropriate in accordance with the command format accepted by the DB management unit 22.

As an example, FIG. 11 illustrates a case in which the variant master table 26 has been read and expanded into the memory 54. In FIG. 11, the variant master table 26 is expanded split into plural tables 102 that, for each variant position, place variant patterns in association with pattern codes. Each of the tables 102 is associated with a different variant ID. Note that although FIG. 11 illustrates a state in which information has been entered into the variant master table 26, at the point when the variant information encoding processing is initially executed, the variant master table 26 is empty.

Figure 12:
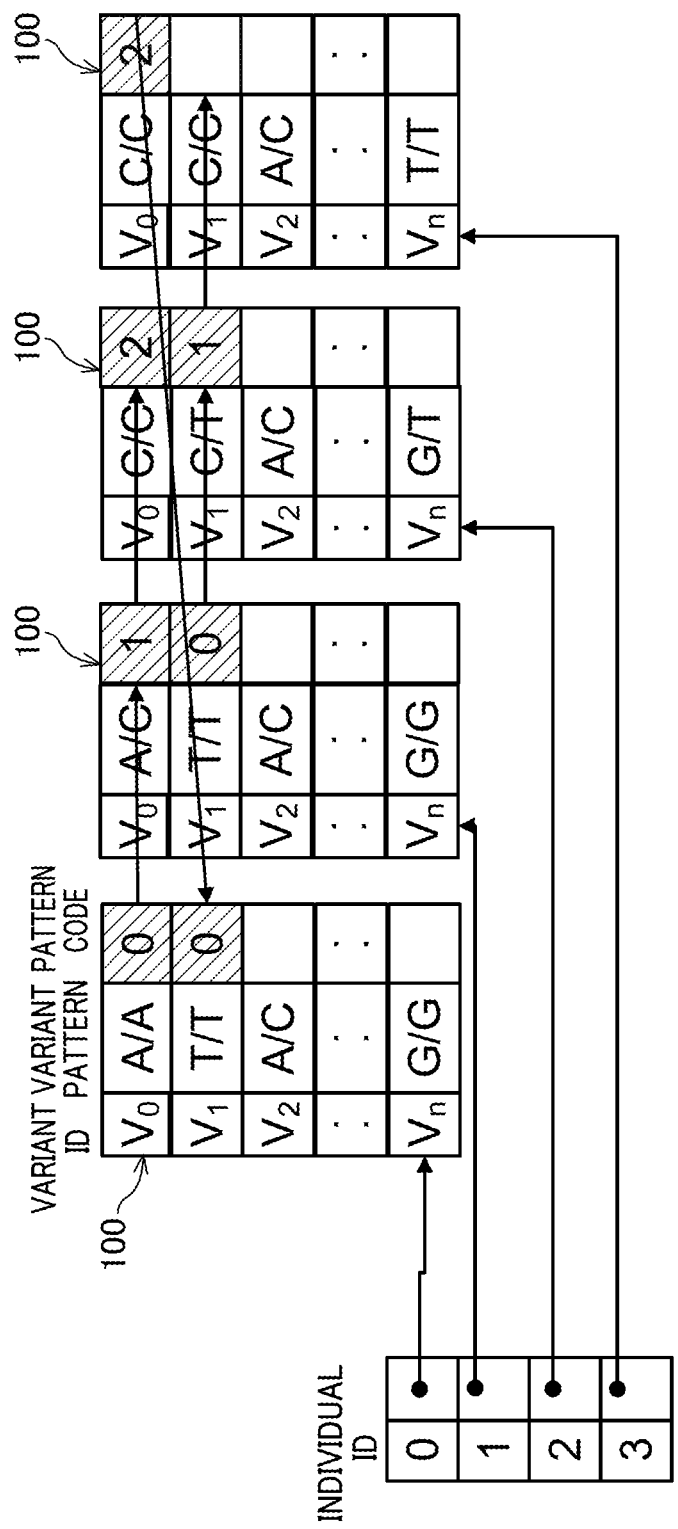
FIG. 12 is a schematic diagram for explaining processing to verify whether or not individual variant patterns included in variant information have been entered into the variant master table.

Next, at step 206, the processors 18 verify whether each variant pattern included in the variant information 100 for individuals im to (i+1)m−1 expanded into the memory 54 at the foregoing step 200 has been entered into the variant master table 26. As an example, FIG. 12 illustrates a case in which variant patterns included in variant information 100 are checked against the variant master table 26 in sequence starting from variant ID=V0 and for each individual, and pattern codes corresponding to variant patterns entered in the variant master table 26 are copied to the variant information 100. Supposing that the information illustrated in FIG. 11 were entered in the variant master table 26, determination would be made that the variant pattern "C/C" at variant ID=V1 in the variant information 100 for individual ID=3 illustrated in FIG. 12 has not been entered in the variant master table 26 illustrated in FIG. 11.

However, at step 206, processing to copy variant patterns entered in the variant master table 26 into the pattern codes is not absolutely necessary. For example, configuration may be such that determination as to whether or not a variant pattern has been entered in the variant master table 26 is sequentially performed for each variant pattern, and processing to store relevant information is performed for those variant patterns determined to be unentered.

At step 208, the processors 18 make a determination as to whether or not any variant patterns that had not been entered in the variant master table 26 were found to be present in the variant pattern verification of step 206. Processing transitions to step 210 in cases in which the determination of step 208 is affirmative.

Figure 13:
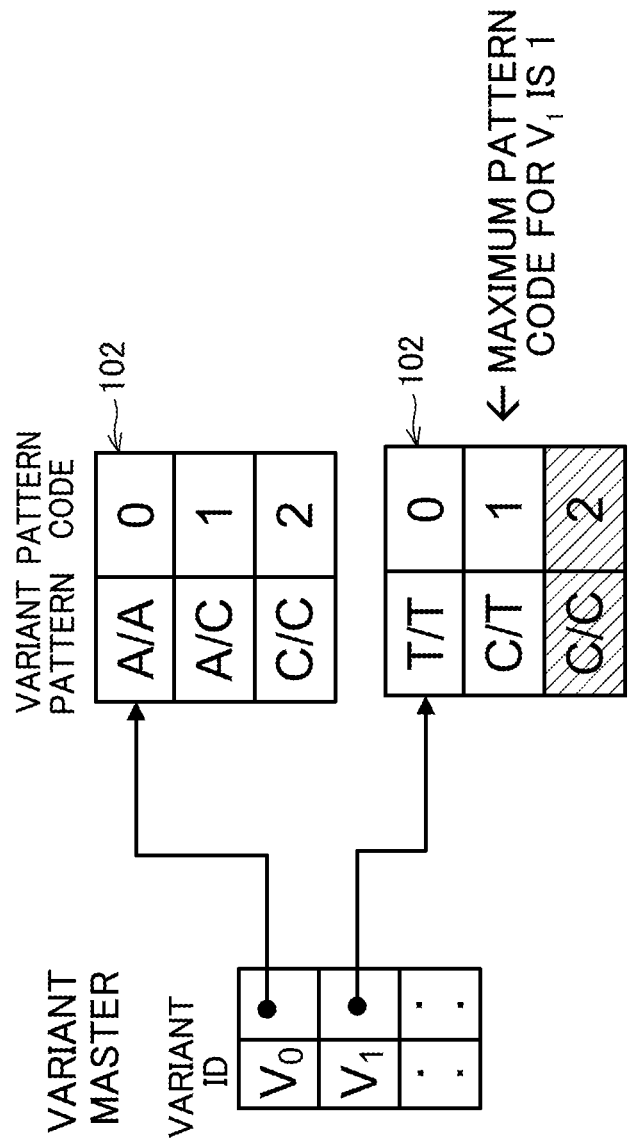
FIG. 13 is a schematic diagram for explaining processing to acquire a pattern code corresponding to a variant pattern not entered in a variant master table.
Figure 14:
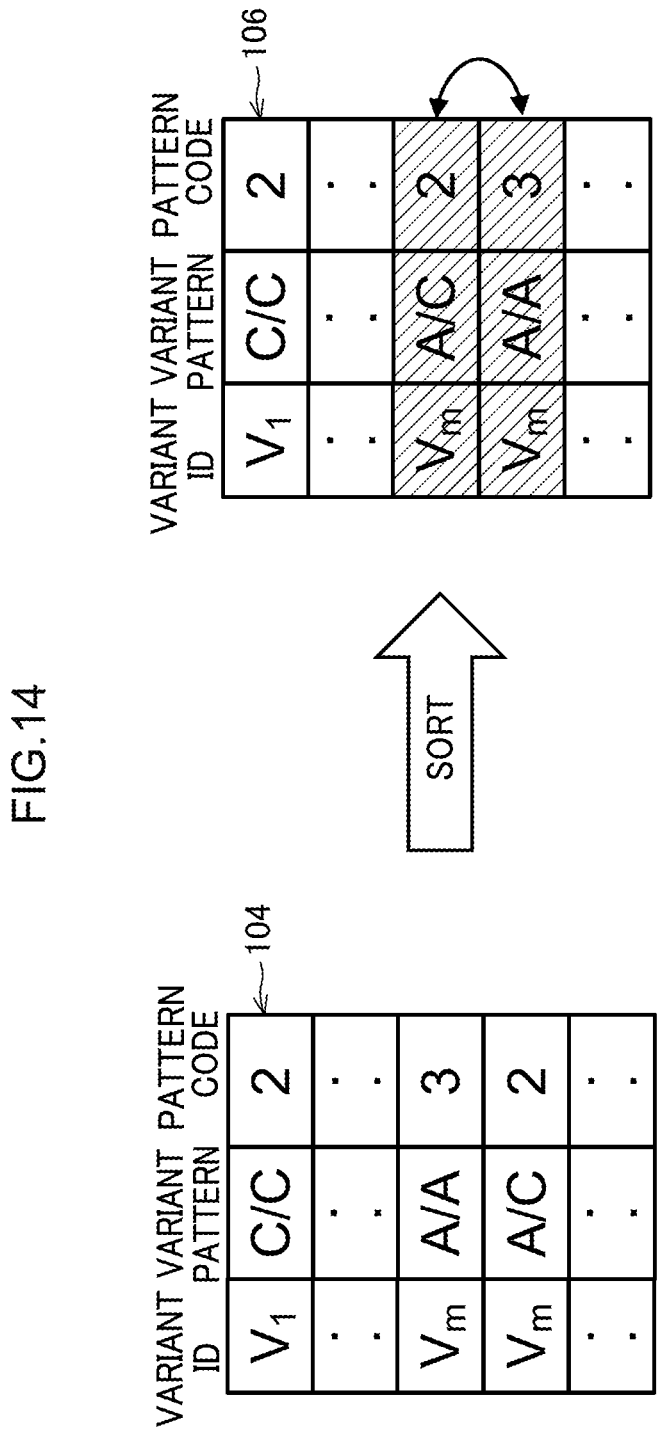
FIG. 14 is a schematic diagram illustrating an unsorted list and a sorted list of information to be added to a variant master table.

At step 210, the processors 18 generate a list of information to be added to the variant master table 26. The list of information to be added has the same number of rows of information as the number of unentered variant patterns. Each row of information in the list of information to be added contains a variant ID, pattern code, and variant pattern corresponding to a variant pattern not entered in the variant master table 26. Note that the variant ID and the variant pattern in a row of information corresponding to a single unentered variant pattern can be acquired from the variant information 100. Further, as illustrated in FIG. 13, for example, the pattern code in a row of information corresponding to a single unentered variant pattern can be obtained by acquiring the maximum value of the respective pattern codes from the tables 102 expanded from the variant master table 26 and adding 1 to the acquired maximum value. In the example of FIG. 13, the maximum value of the pattern codes for variant ID=V1 is "1". Thus, adding 1 to this maximum value results in a value of "2" for the pattern code in a row of information corresponding to the unentered variant pattern "C/C" for variant ID=V1. An unsorted list 104 such as illustrated in the example of FIG. 14 is thereby obtained.

The rows of information included in the list of information to be added generated at step 210 are, for example, arranged by the order of appearance of unentered variant patterns in the variant master table 26 in the variant information 100 of m individuals. Accordingly, at the following step 212, the processors 18 sort the rows of information included in the list of information to be added in ascending order of the values of pairs of variant IDs and pattern codes. For example, in the unsorted list 104 illustrated in FIG. 14, the row of information where variant ID=Vm and pattern code=3 is positioned before the row of information where variant ID=Vm and pattern code=2, but in the sorted list 106 illustrated in FIG. 14 these rows are swapped. The reason for sorting the list of information to be added will be explained later.

Next, at step 214, the processors 18 output a command to the DB management unit 22 instructing the insertion of the first row of information not yet inserted into the variant master table 26 from the sorted list of information to be added 106, such that this row of information is inserted into the variant master table 26. Note that an example of a command for inserting a row of information into the variant master table 26 is as follows for the case in which, for example, variant ID=V1, pattern code=2, and variant pattern="C/C" in the row of information being inserted into the variant master table 26: "INSERT INTO variant_master_tbl VALUES(V1, 2, C/C)". However, there is no limitation to this command, and this command may be modified as appropriate in accordance with the command format accepted by the DB management unit 22.

At step 216, the processors 18 make a determination as to whether or not a reply from the DB management unit 22 has been input in response to the command output at step 214. In cases in which the determination of step 216 is negative, the determination of step 216 is repeated. When a reply from the DB management unit 22 has been input, affirmative determination is made at step 216 and processing transitions to step 218. At step 218, the processors 18 make a determination as to whether or not there has been a notification of a composite primary key constraint violation from the DB management unit 22.

In the following, explanation is first given regarding a case in which a row of information, for which there had been an insertion instruction, is inserted into the variant master table 26 without giving a composite primary key constraint violation notification to the processor 18 that gave the instruction to insert that row of information into the variant master table 26. As an example, FIG. 15 illustrates a case in which the first row of information in a sorted list of information to be added 106 is inserted into the variant master table 26. In cases in which a reply from the DB management unit 22 has been input and there was not a composite primary key constraint violation notification given by the DB management unit 22, the determination of step 218 is negative and processing transitions to step 220.

At step 220, the processors 18 make a determination as to whether or not the insertion of all rows of information included in the list of information to be added to the variant master table 26 is complete. In cases in which negative determination is made at step 220, processing returns to step 214, and the processing of step 214 to step 220 repeats until the determination of step 220 is affirmative. When all rows of information included in the list of information to be added have been inserted into the variant master table 26, affirmative determination is made at step 220 and processing transitions to step 222.

At step 222, similarly to at step 204 described above, the processors 18 output a command to the DB management unit 22 to read the variant master table 26, and the variant master table 26 that has been read via the DB management unit 22 is expanded into the memory 54. At subsequent step 224, the processors 18 output a command to the DB management unit 22 to end the respective transaction. Note that "COMMIT" is one example of a command to end a transaction; however, there is no limitation thereto, and this command may be modified as appropriate in accordance with the command format accepted by the DB management unit 22.

Figure 16:
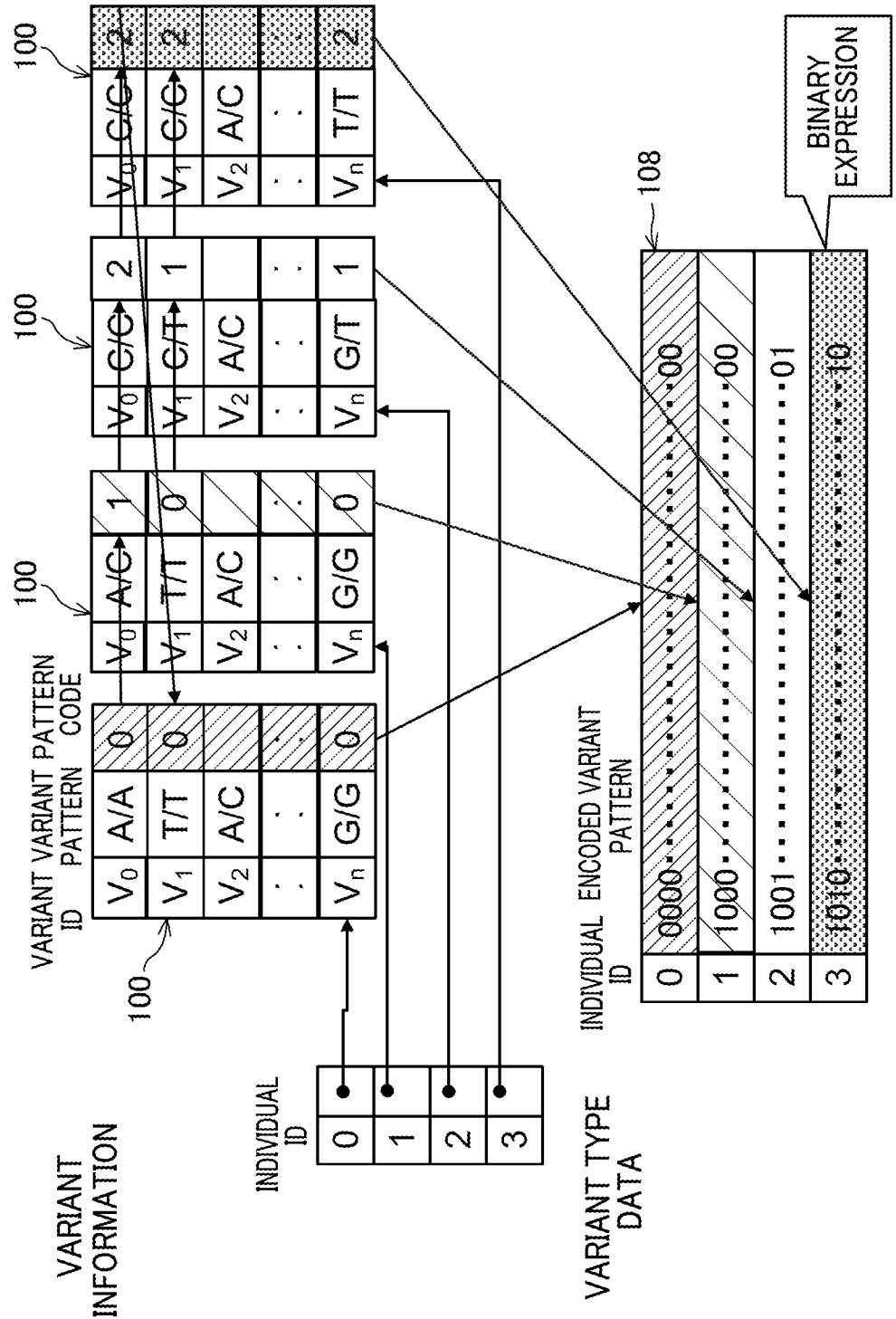
FIG. 16 is a schematic diagram illustrating processing to create variant type information arranged in sequence by a pattern code for each individual corresponding to a variant pattern included in variant information.
Figure 17:
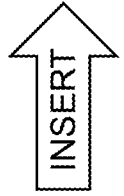
FIG. 17 is a schematic diagram illustrating processing to store variant type information in a variant type storing table.

At step 226, the processors 18 acquire the pattern codes from the variant master table 26 corresponding to each variant pattern included in the variant information 100 for individuals im to (i+1)m−1 subject to processing that has been expanded into the memory 54 at step 200. Next, the processors 18 create variant type information arranged in the sequence of the acquired pattern codes for each individual. FIG. 16 illustrates an example in which pattern codes corresponding to variant patterns included in variant information 100 for each individual have been added to the variant information 100 of each individual, after which the pattern codes are used to create variant type information 108, in which the pattern codes are sequentially arranged, for each individual. As illustrated in the example of FIG. 17 the processors 18 then store the variant type information 108 created for each individual in the variant type storing table 28. Upon performing the processing of step 226, the variant information encoding processing ends.

While the value of the counter i, indicating the number of process (processors 18) activations, is small, most of the variant patterns included in the variant information 100 for individuals im to (i+1)m−1 subject to processing will not have been entered in the variant master table 26. Particularly, when i=0, the variant patterns will not have been entered in the variant master table 26 in any of the activated processes (processors 18).

Thus, while the value of counter i is small, when the plural (Y or fewer) activated processes (processors 18) attempt to insert respective rows of information into the variant master table 26, composite primary key constraint violations will occur at a relatively high frequency for reasons explained later. As a result, while the value of counter i is small, for the portion of the plural activated processes (processors 18) where the counter i has a smaller value at the time of activation (those that were activated earlier), one or more variant pattern is entered for each variant position.

Note that FIG. 18 illustrates the portion of the processes (processors 18) that enter a variant pattern into the variant master table 26 while the value of the counter i is small as processes 0 and 1 in the section labeled "PROPOSED METHOD". In the section labeled "PROPOSED METHOD" in the example of FIG. 18, the number of processes (processors 18) that enter a variant pattern into the variant master table 26 here is equal to 2. However, it goes without saying that a number other than 2 is possible for the number of these processes.

Herein, were each of the activated processors 18 to lock the entire variant master table 26 before updating the variant master table 26, even if the plural processors 18 were operating in parallel, processing by any processor 18 that did not have permission to perform an update would have to wait until the lock was released. Thus, as illustrated in the section labeled "TABLE LOCKING" in FIG. 18, processing (labeled processes 0 to 7 in FIG. 18) performed by plural processors 18 would, in practice, be sequential processing.

In contrast thereto, in the present exemplary embodiment, the variant ID column and the pattern code column in the variant master table 26 set a composite primary key constraint for the variant master table 26, and the plural processors 18 are permitted to update (insert a row of information into) the variant master table 26 in parallel so long as there is not a composite primary key constraint violation. Thus, as the value of the counter i increases, and the number of variant patterns entered into the variant master table 26 grows larger, processing performed by the plural activated processors 18 is executed substantially in parallel, increasing processing efficiency, and thereby reducing processing time. In the section labeled "PROPOSED METHOD" illustrated in FIG. 18, the plural processors 18 activated such that processing is performed substantially in parallel are labeled as processes 2 to 7.

However, in the present exemplary embodiment, updates to the variant master table 26 that violate a composite primary key constraint are eliminated. The section labeled "PROPOSED METHOD" in FIG. 18 illustrates a case in which an update to the variant master table 26 by the processor 18 labeled process 5 violates a composite primary key constraint with respect to an update to the variant master table 26 by the processor 18 labeled process 4. Explanation follows regarding a case in which a row of information to be inserted into the variant master table 26 causes a composite primary key constraint violation.

Consider the case in which the row of information where variant ID=Vm, pattern code=2, and variant pattern="A/C" in a sorted list of information to be added 106 is inserted into a variant master table 26, as illustrated in FIG. 19. In the variant master table 26 illustrated in FIG. 19, a record with a variant ID and pattern code that overlap with that of this row of information, namely, a record where variant ID=Vm, pattern code=2, and variant pattern="A/A", already exists.

Accordingly, when input with a command instructing the insertion of this row of information, the DB management unit 22 detects that the row of information for which the insertion instruction was given may violate a composite primary key constraint. However, until the transaction of the processor 18 that gave the instruction to insert the corresponding records present in the variant master table 26 have ended, a composite primary key constraint violation is not definite. Thus, until the transaction of the processor 18 that gave the instruction to insert the corresponding record ends, the DB management unit 22 withholds its reply to the processor 18 that gave the instruction to insert the row of information violating a composite primary key constraint.

Figure 20:
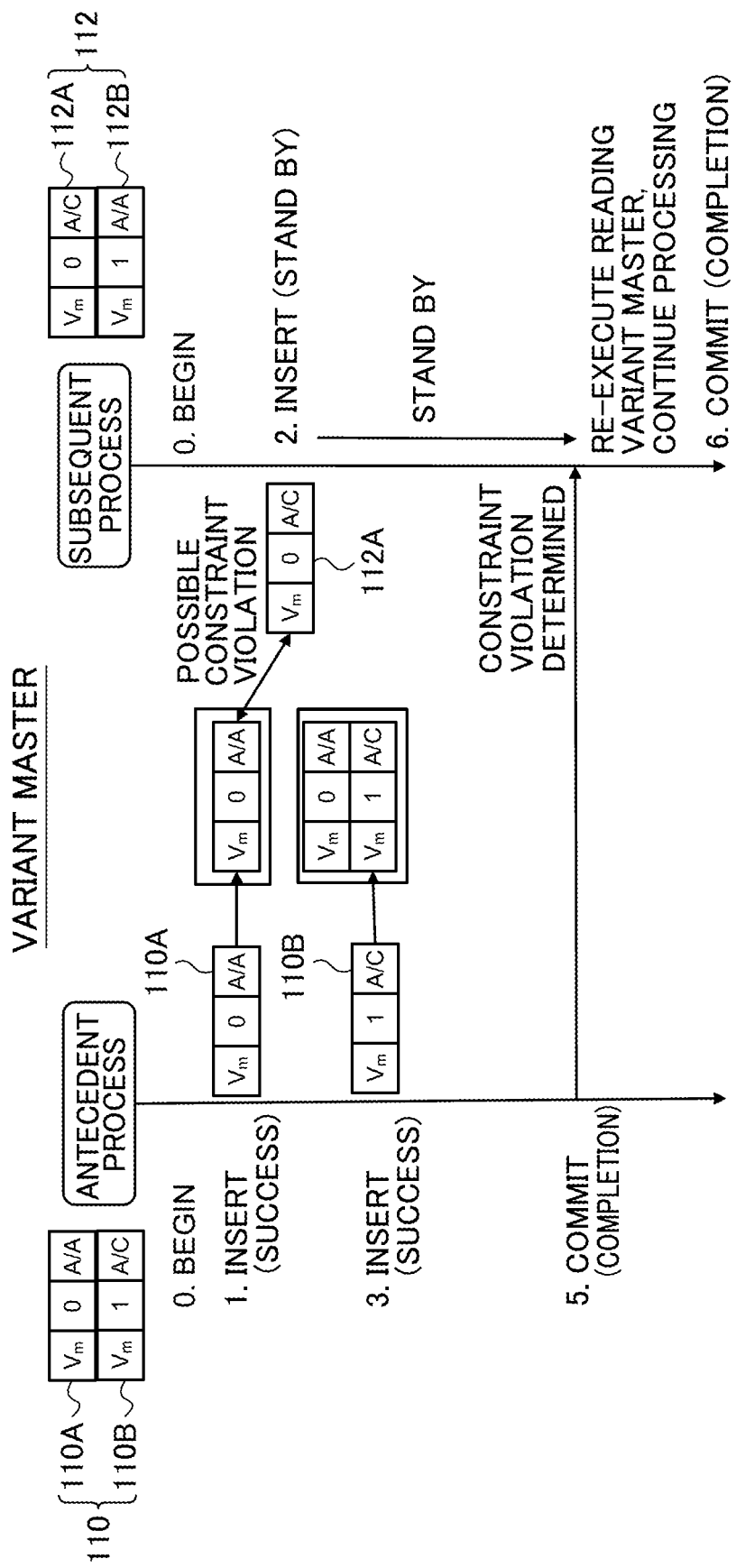
FIG. 20 is a timing chart (for sorting a list of information to be added to a variant master table) explained in an exemplary embodiment.

Additional explanation follows regarding a situation in which a composite primary key constraint violation occurs, with reference to FIG. 20. In FIG. 20, the processor 18 labeled "antecedent process" creates a list 110 containing a row of information 110A and a row of information 110B. In the row of information 110A, variant ID=Vm, pattern code=0, and variant pattern="A/A". In the row of information 110B, variant ID=Vm, pattern code=1, and variant pattern="A/C". The processor 18 labeled "subsequent process" creates a list 112 containing a row of information 112A and a row of information 112B. In the row of information 112A, variant ID=Vm, pattern code=0, and variant pattern="A/C". In the row of information 112B, variant ID=Vm, pattern code=1, and variant pattern="A/A".

In FIG. 20, the variant ID and the pattern code the row of information 110A included in the list 110 created by the processor 18 labeled "antecedent process" overlap with that in the row of information 112A included in the list 112 created by the processor 18 labeled "subsequent process". Note that overlap of variant ID and pattern code occurs when the subsequent process reads the variant master table 26 during the interval between the antecedent process reading the variant master table 26 and the antecedent process inserting the row of information 110A.

As illustrated in FIG. 20, in cases in which the subsequent process attempts to insert the row of information 112A into the variant master table 26 after the antecedent process has inserted the row of information 110A into the variant master table 26, the DB management unit 22 detects a possible composite primary key constraint violation. The DB management unit 22 then withholds its reply to the subsequent process until the transaction of the antecedent process has ended. The reason for this is that the antecedent process may output a command (for example, "rollback") to the DB management unit 22 to cancel the insertion of the row of information into the variant master table 26 due to, for example, the occurrence of a fault, and so insertion of the row of information 110A is not yet definite.

Accordingly, the subsequent process that attempted to insert the row of information 112A into the variant master table 26 stands by until the transaction of the antecedent process ends for a reply from the DB management unit 22. During this interval, provided that a fault or the like does not occur, the antecedent process performs processing including that to insert the row of information 110B into the variant master table 26 before ending its transaction.

When the transaction of the antecedent process has ended, insertion of the rows of information 110A, 110B into the variant master table 26 is definite, and thus the composite primary key constraint violation for the row of information 112A that the subsequent process had attempted to insert into the variant master table 26 is also definite. At this point, the DB management unit 22 sends its reply to notify the subsequent process that there is a composite primary key constraint violation for the row of information 112A.

When the reply comes back from the DB management unit 22 the processor 18 corresponding to the subsequent process makes an affirmative determination at step 216 in FIG. 9, and makes an affirmative determination at step 218, such that processing returns to step 204. In such case, the variant master table 26 is re-read at step 204 and the processing subsequent thereto is performed once again such that the pattern code included in the row of information for which insertion into the variant master table 26 is being attempted is updated to a new pattern code that does not violate a composite primary key constraint. Reoccurrence of a composite primary key constraint violation is thereby suppressed, ensuring that information entered in the variant master table 26 is unique.

Explanation follows regarding the reason why the list of information to be added to the variant master table 26 is sorted at step 212, with reference to FIG. 21. FIG. 21 illustrates a case in which the list 112 of the subsequent process is not sorted, and the order of the rows of information 112A, 112B in the list 112 is reversed from the order illustrated in FIG. 20. Accordingly, in FIG. 21, the subsequent process attempts to insert the row of information 112A into the variant master table 26 after attempting to insert the row of information 112B into the variant master table 26. Note that, although omitted from the explanation relating to FIG. 20, there is also variant ID and pattern code overlap between the row of information 110B included in the list 110 of the antecedent process and the row of information 112B included in the list 112 of the subsequent process.

In the example illustrated in FIG. 21, the subsequent process attempts to insert the row of information 112B into the variant master table 26 after the antecedent process has attempted to insert the row of information 110A into the variant master table 26. A composite primary key constraint violation does not occur for these insertions. However, afterwards, when the antecedent process attempts to insert the row of information 110B into the variant master table 26, the DB management unit 22 detects the possibility of a composite primary key constraint violation with the row of information 112B that had been previously inserted into the variant master table 26 by the subsequent process. Accordingly, the DB management unit 22 withholds its reply to the antecedent process until the transaction of the subsequent process has ended.

Then, when the subsequent process attempts to insert the row of information 112A into the variant master table 26, the DB management unit 22 detects the possibility of a composite primary key constraint violation with the row of information 110A that had been previously inserted into the variant master table 26 by the antecedent process. Accordingly, the DB management unit 22 withholds its reply to the subsequent process until the transaction of the antecedent process has ended. The antecedent process and the subsequent process thus fall into a state known as "deadlock", in which neither can resume processing until the transaction of the other has ended.

In contrast thereto, in the present exemplary embodiment, the list of information to be added to the variant master table 26 is sorted at step 212, and then insertion of the rows of information in the sorted list into the variant master table 26 is attempted in sequence starting from the first row of information not inserted into the variant master table 26. Thus, as illustrated in FIG. 20, the possibility that insertion of a row of information by a processor 18 that started to update the variant master table 26 first results in a composite primary key constraint violation with respect to a row of information that had already been inserted by a processor 18 that started updating the variant master table 26 later is eliminated. This suppresses falling into a deadlocked state.

Note that as the value of the counter i increases, and the number of times that variant information encoding processing has been executed by the processors 18 grows larger, the frequency of appearance of variant patterns not entered in the variant master table 26 will drop, and the frequency of negative determination at step 208 will increase. Processing transitions to step 224 in cases in which negative determination is made at step 208, and the respective transaction will end without inserting a row of information into the variant master table 26. Thus, as the value of the counter i increases, composite primary key constraint violations occur less frequently, and processing efficiency is further increased.

As described above, in the present exemplary embodiment, the variant information processing device 12 includes plural processors 18 that operate in parallel, and each of the plural processors 18 reads variant information differing from that of the others. The variant information includes a variant pattern for each variant position. The variant master table 26 includes a column for variant IDs, a column for variant patterns appearing at a respective variant position, and a column for pattern codes allocated to a respective variant pattern. A composite primary key constraint for the variant master table 26 is set by the variant position ID column and the pattern code column. The processors 18 perform the following processing in cases in which a variant pattern at a variant position included in the read variant information has not been entered into the variant master table 26. Namely, each processor 18 attempts to insert, into the variant master table 26, a row of information including the unentered variant pattern, the corresponding variant ID, and a pattern code that has been allocated based on and the variant master table 26. In cases in which the row of information that a processor 18 has attempted to insert violates the composite primary key constraint for another row of information that had previously been inserted by another processor 18, the processor 18 reattempts to insert an updated row of information in which the pattern code included in the row of information that it attempted to insert has been changed. Then, the processor 18 encodes the variant information based on information entered in the variant master table 26. This enables the uniqueness of information to be ensured in cases in which updates to the variant master table 26 are performed in parallel, while also suppressing a reduction in processing efficiency.

Further, in the present exemplary embodiment, the processors 18 perform the following processing in cases in which a row of information for which insertion was attempted violates a composite primary key constraint for a row of information that had previously been inserted by another processor 18. Namely, until a row of information is successfully inserted, the respective processor 18 keeps reattempting to insert an updated row of information in which the pattern code included in the row of information that it previously attempted to insert has been changed. This enables the reliable insertion, into the variant master table 26, of rows of information having a variant pattern, and corresponding variant position ID, not entered in the variant master table 26 and in which the pattern code does not violate a composite primary key constraint.

Further, in the present exemplary embodiment, the processors 18 perform the following processing in cases in which plural variant patterns not entered in the variant master table 26 are included in the read variant information. Namely, the respective processor 18 attempts to insert plural rows of information corresponding to the variant patterns into the variant master table 26 in ascending order of the values of pairs of variant IDs and pattern codes. This enables plural processors 18 operating in parallel to be suppressed from becoming deadlocked.

Further, in the present exemplary embodiment, the processors 18 attempt to insert respective rows of information into the variant master table 26 via the DB management unit 22. The DB management unit 22 performs the following processing in cases in which, after a first processor 18 has attempted to insert a first row of information, a second processor 18 has attempted to insert a second row of information that violates a composite primary key constraint for the first row of information. Namely, the DB management unit 22 notifies the first processor 18 that the insertion of the first row of information was successful, and after the transaction of the first processor 18 has ended, the DB management unit 22 notifies the second processor 18 that the second row of information violates a composite primary key constraint. Employing existing functionality of the DB management unit 22 in this manner enables the uniqueness of information in the variant master table 26 to be ensured using a simple configuration and simple processing.

Note that in the above, explanation was given in which the rows of information included in the list of information to be added are sorted such that the values of pairs of variant IDs and pattern codes are arranged in ascending order, and the rows of information included in the sorted list of information to be added are inserted into the variant master table 26 in sequence from the top. However, there is no limitation thereto. For example, the rows of information included in the list of information to be added may be sorted such that the values of pairs of variant IDs and pattern codes are arranged in descending order, and the rows of information included in the sorted list of information to be added are inserted into the variant master table 26 in sequence from the bottom.

Further, configuration may be such that rows of information in the list of information to be added are not sorted, and each time a row of information is inserted into the variant master table 26, the uninserted row of information with the smallest values for its variant ID and pattern code pair is found in the list of information to be added, and then inserted. Discernment between which individual rows of information included in the list of information to be added have been inserted and which have not been inserted may be made by appending a flag or the like to rows of information, out of the rows of information included in the list of information to be added, that have been inserted into the variant master table 26.

Further, although explanation was given regarding the acquisition of a maximum value of the pattern codes entered in the variant master table, and configuring a new pattern code as a value obtained by adding 1 to the acquired maximum value, no particular description was given regarding a number of bits for the pattern codes. As proposed by the present applicants in Japanese Patent Application 2016-30268, for example, the number of bits for pattern codes may initially be set to 2 bits, and this bit value increased in 2-bit increments each time a variant pattern appears that causes the number of variant pattern types to exceed a value that can be expressed by the current number of bits. As also proposed in Japanese Patent Application 2016-30268, for variant positions where the number of bits of the pattern code is greater than 2, configuration may be such that the additional bit values are stored at the end of the respective variant type information.

Moreover, although the present invention has been explained as applied to variant information for humans, there is no limitation thereto, and application may be made to organisms other than humans.

Moreover, in the above, explanation was given in which the variant information processing program 70, which is an example of an information processing program of the present invention, is stored (installed) in the storage section 56 in advance. However, the information processing program of the present invention may also be provided stored on a recording medium such as a CD-ROM, DVD-ROM, or memory card.

In genetic information (DNA base sequences), there are tens of millions of locations where differences between individuals may arise, namely, where genetic information differs depending on the individual (referred to as variant positions). The genetic information (variant patterns) at some of these variant positions may be correlated with the incidence of certain conditions. Research and the like is therefore ongoing to analyze which variant positions, and corresponding variant patterns, are correlated with the incidence of certain conditions by testing for whether or not there is a significant difference in the frequency of appearance of each variant pattern at respective variant positions between a group of individuals that have a certain condition and a group of individuals that do not have the condition, for example.

When, for example, performing analysis of genetic information as in the research mentioned in Related Patent Documents, per-individual variant information is prepared by extracting variant patterns at each variant position from the genetic information of each individual and sequentially arranging the per-individual variant information. However, in cases in which variant information for a large number of individuals is handled, efficient processing is desired so as to reduce processing time. It is conceivable to perform subsequent processing, such as tallying, after reducing the amount of data by rewriting (encoding) the variant patterns at each variant position included in the variant information into a code expressing the variant pattern.

However, in the variant information for all individuals subject to processing, at the point when encoding of variant information begins, what variant patterns will appear at individual variant positions and which types of variant patterns will appear at each of the individual variant position are both unknown. Thus, when encoding variant information, for each variant position, to allocate new codes to newly appeared variant patterns and add these codes to a table a table that is entered with correspondence relationships between the variant patterns at each variant position and the codes needs to be generated and updated. This table is referred to below as a "variant master table".

Further, in order to make processing more efficient, it is effective to operate plural processes in parallel that each read differing variant information, update the variant master table, and encode their respective variant information. However, in cases in which plural processes operating in parallel each perform an update to the variant master table, the updates to the variant master table may conflict such the information entered in the variant master table loses its uniqueness. In cases in which a single processes is given permission to update the variant master table so as not lose the uniqueness of the information, updating the variant master table by the plural processes becomes, in practice, sequential processing, resulting in reduced processing efficiency.

Although the first technology and the second technology are technologies to ensure the uniqueness of information, they do not consider cases in which table updates are performed by, for example, plural processes or transactions in parallel. For example, in the first technology, in cases in which a DB operation that violates a unique constraint is received from a second transaction before giving a reply with respect to a first DB operation from a first transaction, were violation counters to be provided at the DB level, the reply would be determined as stating that there is a violation. Further, were violation counters to be provided at the transaction level, then there would be a mismatch between the respective violation counters for the transactions.

In the second technology, sequential commands from a single client are entered into a difference table as difference information, and an assumption is made that while any given client is committing an operation, other clients are not able to reference or update data. Thus, with the second technology, referencing or updating data using plural clients becomes, in practice, sequential processing, resulting in reduced processing efficiency.

One aspect has the excellent advantageous effect of enabling the uniqueness of information to be ensured in cases in which updates to a variant master table are performed in parallel, while also suppressing a reduction in processing efficiency.

All cited documents, patent applications, and technical standards mentioned in the present specification are incorporated by reference herein to the same extent as if each individual cited document, patent application, or technical standard was specifically and individually indicated to be incorporated by reference.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An information processing device comprising:
   a memory that is configured to store a variant master table that includes a column for variant position identifying information, a column for a variant pattern appearing at a respective variant position, and a column for a code allocated to the respective variant pattern, and that has a composite primary key constraint set by the column for the variant position identifying information and the column for the code; and
   a plurality of respective processors coupled to the memory and that is configured to operate in parallel, each of the plurality of processors being configured to execute a procedure, the procedure comprising:
      the respective processors reading variant information, the variant information including a variant pattern for each variant position and differing between the processors;
      in cases in which a variant pattern at a variant position included in the read variant information has not been entered into the variant master table, the respective processors attempting to insert, into the variant master table, a row of information including the unentered variant pattern, corresponding variant position identifying information, and a code allocated based on the variant master table;
      in cases in which the row of information for which insertion was attempted violates a composite primary key constraint for a row of information that had previously been inserted by another processor other than the respective processors, the respective processors reattempting to insert an updated row of information in which the code included in the row of information for which insertion was attempted has been changed; and
      the respective processors encoding the variant information based on information entered into the variant master table.

2. The information processing device of claim 1, wherein, in cases in which the row of information for which insertion was attempted violates a composite primary key constraint for a row of information that had previously been inserted by the other processor, until a row of information is successfully inserted, the respective processors keep reattempting to insert an updated row of information in which the code included in the row of information for which insertion was attempted has been changed.

3. The information processing device of claim 1, wherein, in cases in which plural variant patterns not entered into the variant master table are included in the read variant information, the respective processors attempt to insert plural rows of information corresponding to the variant patterns into the variant master table in ascending order of values of pairs of the respective variant position identifying information and the respective code.

4. The information processing device of claim 2, wherein, in cases in which plural variant patterns not entered into the variant master table are included in the read variant information, the respective processors attempt to insert plural rows of information corresponding to the variant patterns into the variant master table in ascending order of values of pairs of the respective variant position identifying information and the respective code.

5. The information processing device of claim 1, wherein:
the processors each attempt to insert their respective rows of information into the variant master table via a management unit; and
in cases in which, after a first processor has attempted to insert a first row of information, a second processor has attempted to insert a second row of information that violates a composite primary key constraint for the first row of information, the management unit notifies the first processor that the insertion of the first row of information was successful, and after a transaction of the first processor has ended, the management unit notifies the second processor that the second row of information violates a composite primary key constraint.

6. The information processing device of claim 2, wherein:
the processors each attempt to insert their respective rows of information into the variant master table via a management unit; and
in cases in which, after a first processor has attempted to insert a first row of information, a second processor has attempted to insert a second row of information that violates a composite primary key constraint for the first row of information, the management unit notifies the first processor that the insertion of the first row of information was successful, and after a transaction of the first processor has ended, the management unit notifies the second processor that the second row of information violates a composite primary key constraint.

7. An information processing method that causes each of a plurality of processors that is configured to operate in parallel and coupled to a memory to execute a procedure,
the memory being configured to store a variant master table that includes a column for variant position identifying information, a column for a variant pattern appearing at a respective variant position, and a column for a code allocated to the respective variant pattern, and that has a composite primary key constraint set by the column for the variant position identifying information and the column for the code, and
the procedure comprising, by the respective processors:
reading variant information, the variant information including a variant pattern for each variant position and differing between the processors;
in cases in which a variant pattern at a variant position included in the read variant information has not been entered into the variant master table, attempting to insert, into the variant master table, a row of information including the unentered variant pattern, corresponding variant position identifying information, and a code allocated based on the variant master table;
in cases in which the row of information for which insertion was attempted violates a composite primary key constraint for a row of information that had previously been inserted by another processor other than the respective processors, reattempting to insert an updated row of information in which the code included in the row of information for which insertion was attempted has been changed; and
encoding the variant information based on information entered into the variant master table.

8. The information processing method of claim 7, wherein, in cases in which the row of information for which insertion was attempted violates a composite primary key constraint for a row of information that had previously been inserted by the other processor, until a row of information is successfully inserted, the respective processors keep reattempting to insert an updated row of information in which the code included in the row of information for which insertion was attempted has been changed.

9. The information processing method of claim 7, wherein, in cases in which plural variant patterns not entered into the variant master table are included in the read variant information, the respective processors attempt to insert plural rows of information corresponding to the variant patterns into the variant master table in ascending order of values of pairs of the respective variant position identifying information and the respective code.

10. The information processing method of claim 8, wherein in cases in which plural variant patterns not entered into the variant master table are included in the read variant information, the respective processors attempt to insert plural rows of information corresponding to the variant patterns into the variant master table in ascending order of values of pairs of the respective variant position identifying information and the respective code.

11. The information processing method of claim 7, wherein:
the processors each attempt to insert their respective rows of information into the variant master table via a management unit; and
in cases in which, after a first processor has attempted to insert a first row of information, a second processor has attempted to insert a second row of information that violates a composite primary key constraint for the first row of information, the management unit notifies the first processor that the insertion of the first row of information was successful, and after a transaction of the first processor has ended, the management unit notifies the second processor that the second row of information violates a composite primary key constraint.

12. The information processing method of claim 8, wherein:
the processors each attempt to insert their respective rows of information into the variant master table via a management unit; and
in cases in which, after a first processor has attempted to insert a first row of information, a second processor has attempted to insert a second row of information that violates a composite primary key constraint for the first row of information, the management unit notifies the first processor that the insertion of the first row of information was successful, and after a transaction of the first processor has ended, the management unit notifies the second processor that the second row of information violates a composite primary key constraint.

13. A non-transitory computer-readable storage medium having stored therein an information processing program for causing a computer to execute a procedure and a variant master table,
the computer including a plurality of processors that is configured to operate in parallel and coupled to the computer-readable storage medium, and
the variant master table including a column for variant position identifying information, a column for a variant pattern appearing at a respective variant position, and a column for a code allocated to the respective variant pattern, and having a composite primary key constraint set by the column for the variant position identifying information and the column for the code, and the procedure comprising, by the respective processors:
- reading variant information, the variant information including a variant pattern for each variant position and differing between the processors;
- in cases in which a variant pattern at a variant position included in the read variant information has not been entered into the variant master table, attempting to insert, into the variant master table, a row of information including the unentered variant pattern, corresponding variant position identifying information, and a code allocated based on the variant master table;
- in cases in which the row of information for which insertion was attempted violates a composite primary key constraint for a row of information that had previously been inserted by another processor other than the respective processor, reattempting to insert an updated row of information in which the code included in the row of information for which insertion was attempted has been changed; and
- encoding the variant information based on information entered into the variant master table.

14. The non-transitory computer-readable storage medium of claim 13, wherein, in cases in which the row of information for which insertion was attempted violates a composite primary key constraint for a row of information that had previously been inserted by the other processor, until a row of information is successfully inserted, the respective processors keep reattempting to insert an updated row of information in which the code included in the row of information for which insertion was attempted has been changed.

15. The non-transitory computer-readable storage medium of claim 13, wherein, in cases in which plural variant patterns not entered into the variant master table are included in the read variant information, the respective processors attempt to insert plural rows of information corresponding to the variant patterns into the variant master table in ascending order of values of pairs of the respective variant position identifying information and the respective code.

16. The non-transitory computer-readable storage medium of claim 14, wherein, in cases in which plural variant patterns not entered into the variant master table are included in the read variant information, the respective processors attempt to insert plural rows of information corresponding to the variant patterns into the variant master table in ascending order of values of pairs of the respective variant position identifying information and the respective code.

17. The non-transitory computer-readable storage medium of claim 13, wherein:
- the processors each attempt to insert their respective rows of information into the variant master table via a management unit; and
- in cases in which, after a first processor has attempted to insert a first row of information, a second processor has attempted to insert a second row of information that violates a composite primary key constraint for the first row of information, the management unit notifies the first processor that the insertion of the first row of information was successful, and after a transaction of the first processor has ended, the management unit notifies the second processor that the second row of information violates a composite primary key constraint.

18. The non-transitory computer-readable storage medium of claim 14, wherein:
- the processors each attempt to insert their respective rows of information into the variant master table via a management unit; and
- in cases in which, after a first processor has attempted to insert a first row of information, a second processor has attempted to insert a second row of information that violates a composite primary key constraint for the first row of information, the management unit notifies the first processor that the insertion of the first row of information was successful, and after a transaction of the first processor has ended, the management unit notifies the second processor that the second row of information violates a composite primary key constraint.

* * * * *